United States Patent
Chen et al.

(10) Patent No.: US 8,232,088 B2
(45) Date of Patent: Jul. 31, 2012

(54) GENETICALLY ENGINEERED HERBICIDE RESISTANCE FOR MAINTAINING AXENIC CULTURES

(75) Inventors: Ofra Chen, Rehovot (IL); Shai Einbinder, Hofit (IL); Daniella Schatz, Givataim (IL); Doron Eisenstadt, Haifa (IL); Jonathan Gressel, Rehovot (IL)

(73) Assignee: Transalgae Ltd, Rehovot (IL)

( * ) Notice: Subject to any disclaimer, the term of this patent is extended or adjusted under 35 U.S.C. 154(b) by 375 days.

(21) Appl. No.: 12/584,559

(22) Filed: Sep. 8, 2009

(65) Prior Publication Data

US 2010/0068816 A1 Mar. 18, 2010

Related U.S. Application Data

(60) Provisional application No. 61/191,167, filed on Sep. 5, 2008.

(51) Int. Cl.
*C12N 1/12* (2006.01)
*C12N 1/20* (2006.01)

(52) U.S. Cl. .................. 435/252.1; 435/252.3

(58) Field of Classification Search .......... None
See application file for complete search history.

(56) References Cited

U.S. PATENT DOCUMENTS

| 5,910,626 | A | 6/1999 | Haselkorn |
| 7,285,701 | B2 | 10/2007 | Kakefuda |
| 2007/0074303 | A1* | 3/2007 | McCutchen et al. .......... 800/278 |
| 2007/0178451 | A1 | 8/2007 | Deng et al. |

FOREIGN PATENT DOCUMENTS

| EP | 0244234 | 11/1987 |
| EP | 0519229 | 12/1992 |
| WO | WO94/25583 | 11/1994 |
| WO | WO97/02753 | 1/1997 |
| WO | WO97/08325 | 3/1997 |
| WO | WO97/28243 | 8/1997 |

OTHER PUBLICATIONS

Michel, A. e tal. 2004. Somatic mutation-mediated evolution of herbicide resistance . . . Molec. Ecology 12: 3229-3237.
Windhoevel, U. et al. 1994. Expression of *Erwinia uredovora* Phytoene Desaturase in Synechochoccus . . . Plant Physiol. 104: 119-125.

* cited by examiner

*Primary Examiner* — Albert Navarro
(74) *Attorney, Agent, or Firm* — Graeser Associates International Inc; Dvorah Graeser

(57) ABSTRACT

This disclosure provides herbicide resistant algae and cyanobacteria. This disclosure also provides a method to cultivate algae and cyanobacteria in axenic cultures without contaminating species. Moreover, this disclosure provides transgenic algal and cyanobacterial cells that are capable of high production in high light intensities as typically applied in cultivation. Furthermore, a novel transformation method is provided for algal cells.

16 Claims, 14 Drawing Sheets

GENETICALLY ENGINEERED HERBICIDE RESISTANCE FOR MAINTAINING AXENIC CULTURES

PRIORITY

This application claims priority of U.S. Provisional Patent No. 61/191,167 filed on Sep. 5, 2008.

SEQUENCE LISTING

This application contains sequence data provided on a computer readable diskette and as a paper version. The paper version of the sequence data is identical to the data provided on the diskette.

FIELD OF THE INVENTION

This invention relates to cultivation of algae and cyanobacteria. More specifically this invention relates to methods to maintain axenic cultures. The invention relates to management of algal culture by means of genetic modification

BACKGROUND OF THE INVENTION

A major problem in the commercial cultivation of algae and cyanobacteria in axenic culture in bioreactors or open or closed ponds is that they can become contaminated by other, highly competitive but unwanted species of algae and cyanobacteria, fungi and bacteria, as well as by rotifers and other zooplankton that devour the desired species in the cultures. (Sheehan et al. 2004). Fluridone is the only USEPA-approved systemic herbicide that is commonly used for control of aquatic weeds (but not algae) in large bodies of water. It is a noncompetitive inhibitor of the enzyme phytoene desaturase (PDS), which is one of the first dedicated enzymes of the plant carotenoid biosynthesis pathway. Under high light intensities, carotenoids stabilize the photosynthetic apparatus by quenching the excess excitation energy; therefore, inhibition of phytoene desaturase decreases colored carotenoid concentration and causes photo-bleaching of green tissues (Böger and Sandmann 1998).

The pds gene was cloned from the herbicide-susceptible as well as from the recently-evolved, herbicide-resistant biotypes of the water weed hydrilla [*Hydrilla verticillata* (Lf) Royle]. Three separate and independent single-point mutations of the codon 304 encoding for Arg ($Arg_{304}$) in pds were identified in the resistance biotypes (Michel et. al., 2004; Michel et. al., 2004 Patent application WO/2004/007691). The codon usage for $Arg_{304}$ in the wild-type *Hydrilla* is CGT and single-point mutations yielding either Ser (AGT), Cys (TGT), or His (CAT) substitutions were identified in the fluridone resistance biotypes of *Hydrilla*. The resistant biotypes had biomass and-β carotene accumulations of up to 72% and 77% of the content in untreated plants, respectively, while in the susceptible population, fluridone strongly inhibited biomass accumulation and β-carotene accumulation, showing only 10% of the levels found in untreated plants (Michel, et al. 2004). Many fungi and bacteria that synthesize carotenoids as a photoprotectant are sensitive to PDS inhibitors.

Protoporphyrinogen oxidase (PPO; protox) is the last common enzyme in the tetrapyrrole biosynthetic pathway that produces heme and chlorophyll (Beale & Weinstein, 1990). In plants chlorophyll biosynthesis takes place exclusively in plastids, whereas heme is produced in both plastids and mitochondria. In both organelles, PPO converts protoporphyrinogen IX (protogen IX) to protoporphyrin IX (proto IX). Two different nuclear genes, PPX1 and PPX2, encode plastid and mitochondrial PPO isozymes, respectively. When susceptible plants are treated with PPO inhibitors, the substrate of PPO, protogen IX, accumulates and is exported from the organelles into the cytoplasm where herbicide-insensitive peroxidase-like enzymes in the plasma membrane convert it to proto IX. Proto IX accumulates in the cytoplasm and, in the presence of light, induces the formation of singlet oxygen that is damaging to cell membranes.

Herbicides that act by inhibiting protoporphyrinogen oxidase are widely used to control weeds in a variety of crops. The first weed to evolve resistance to PPO-inhibiting herbicides was *Amaranthus tuberculatus*, a problematic weed in the midwestern United States that previously had evolved multiple resistances to herbicides inhibiting two other target sites (Lermontova et. al., 1997; Watanabe et. al., 2001). Evaluation of a PPO inhibitor-resistant *A. tuberculatus* biotype revealed that resistance was an incompletely dominant trait conferred by a single, nuclear gene. Three genes predicted to encode PPO were identified in *A. tuberculatus*. One gene from the resistant biotype, designated PPX2L, contained a codon deletion that was shown to confer resistance by complementation of a hemG mutant strain of *Escherichia coli* grown in the presence and absence of the PPO inhibitor lactofen. PPX2L is predicted to encode both plastid- and mitochondria-targeted PPO isoforms, allowing a mutation in a single gene to confer resistance to two herbicide target sites. Unique aspects of the resistance mechanism include an amino acid deletion, rather than a substitution, and the dual-targeting nature of the gene, which may explain why resistance to PPO inhibitors has been rare (Patzoldt et. al., 2006; Gressel and Levy 2006; Tranel et al., 2007).

Even if fluridone/flurochloridone and protox-inhibiting herbicides are known, their use in algal or cyanobacterial culture has not been possible because the cultured photosynthetic algae or cyanobacteria would also be killed. Moreover, there is an unsolved problem of contamination of alga culture ponds and bioreactors with unwanted species such as rotifers and other zooplankton, which are not controlled by phytoene desaturase or protox-inhibiting algae. This disclosure provides solution to each of these unsolved contamination problems.

SUMMARY OF THE INVENTION

To overcome these problems this invention provides algae and cyanobacteria that are genetically-engineered with herbicide resistance genes and cultured under elevated carbon dioxide conditions to allow control of specific algae and cyanobacteria species as well as zooplankton. Application of small amounts of these herbicides singly or as a cocktail to the cultured ponds will prevent the growth of unwanted algae, cyanobacteria, fungi and bacteria and their establishment in the ponds, and cultivation at elevated carbon dioxide levels will control the rotifers and other zooplankton Accordingly, the present invention relates to transgenic algae and cyanobacteria that are capable of being cultivated in ponds where wild type cells and unwanted species can easily be controlled.

The present invention also relates transgenic algae and cyanobacteria that are capable of high production in artificial conditions, but which have impaired capability to compete in natural environments.

The present invention further relates to herbicide resistance genes that are either co-transformed with other genes such as genes encoding modified protein and starch synthesis, reduced Rubisco, reduced antenna size or modified lipid biosynthesis or the genes are constructed together on the same plasmid and are transformed to the desired algae and cyanobacteria. New genes can be also introduced in the background of transgenic algae that were transformed with the mentioned genes.

The present invention also relates to a novel transformation method for algae and cyanobacteria.

A. By electroporation: The numbers represent the following: wild type (1), transformed 1 (2), transformed 3 (2), positive control (the transformed plasmid) (4), no template DNA (5), and molecular weight marker (6).

B. By microporation, showing the insertion of the pds gene into the transformed cells. Pos—positive control; NTC—no template control; WT—wild type-DNA—colonies that were not transformed with DNA and grew on the selection plates; 1-19—transformed colonies.

Figure 6:
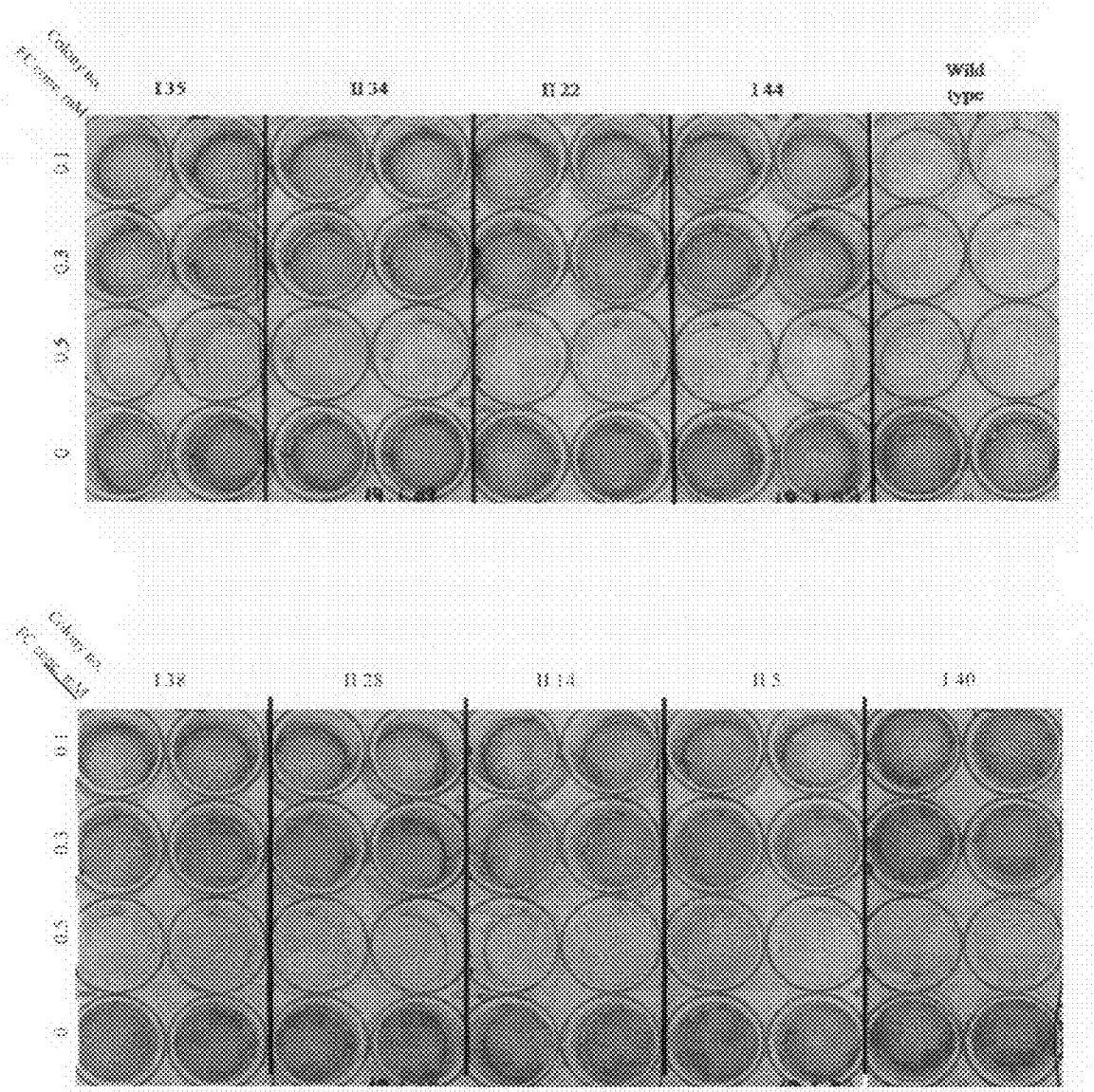

FIG. 6: Dose response for the Chlamydomonas pds transformants colonies. Wild type and pds transformed colonies (pds I35, pds II34, pds II 22, pds I44, pds I38, pds II28, pds II14, pds I15, pds I40) were inoculated at $OD_{750}$=0.1 and flurochloridone was applied at the concentrations of 0.1, 0.3 and 0.5 µM. Cultures were grown for a week before picture was taken.

Figure 7:
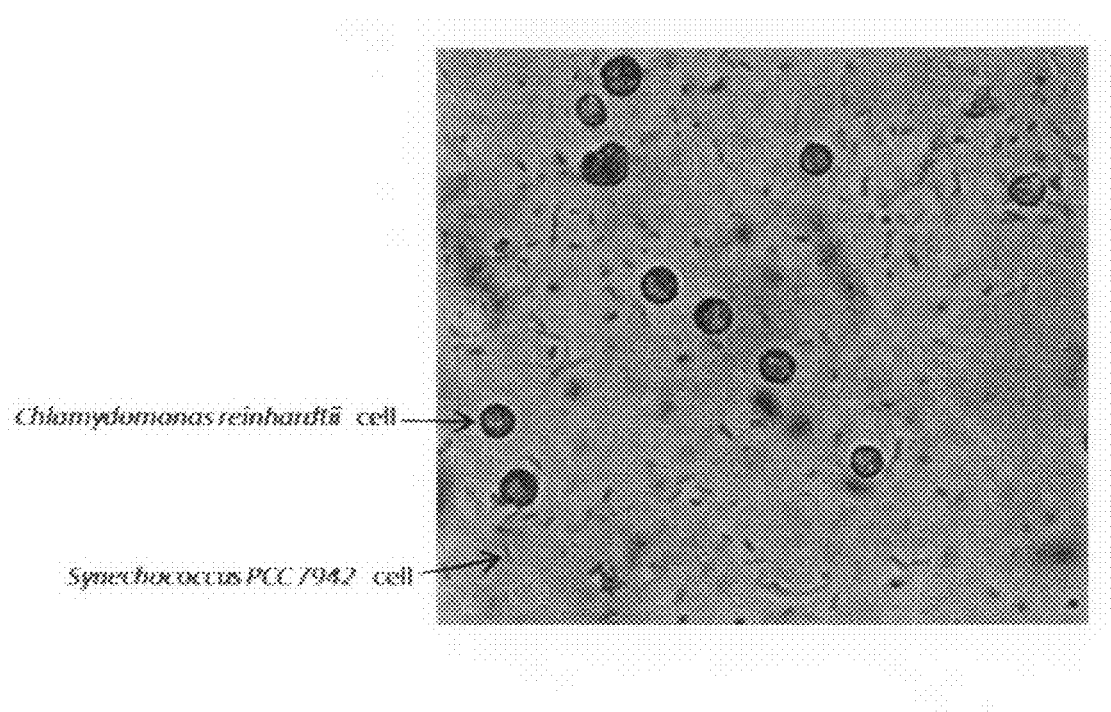

FIG. 7: Mixed culture of the alga Chlamydomonas reinhardtii and the cyanobacterium Synechococcus PCC 7942 as visualized under the microscope.

Figure 8A:
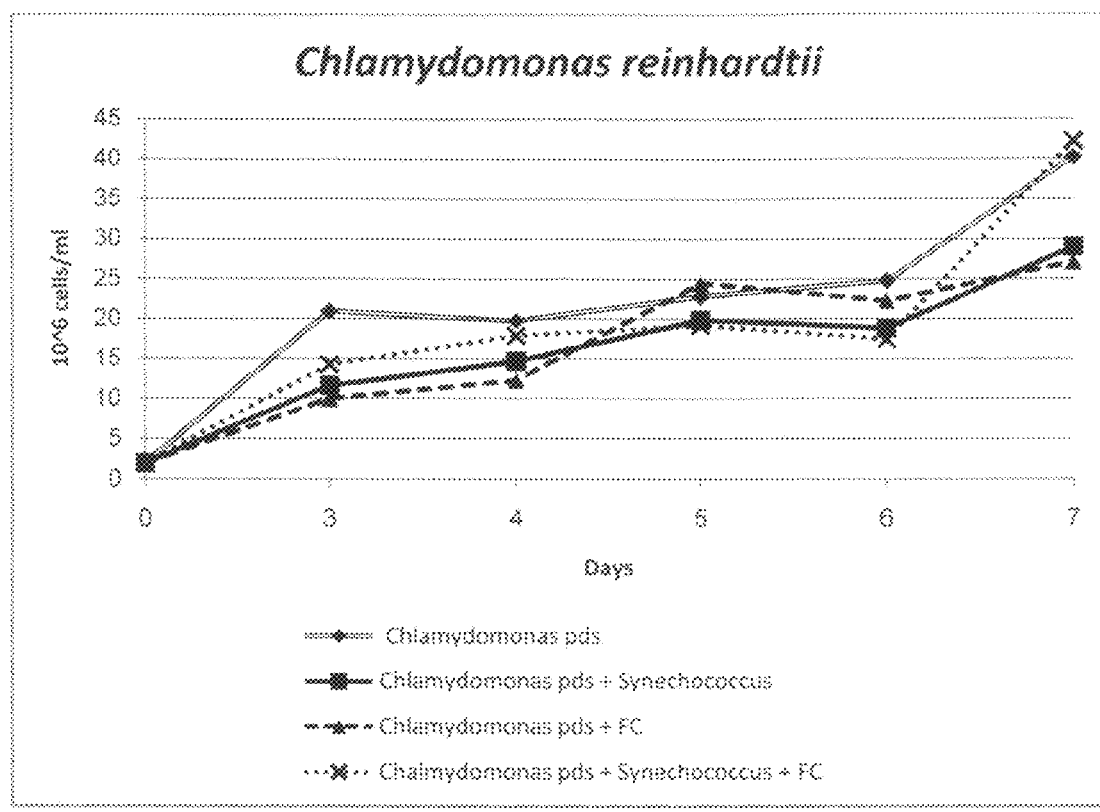

FIGS. 8A and B: Contamination test of Chlamydomonas pds transformant II5 versus the cyanobacterium Synechococcus PCC 7942. Chlamydomonas transformants and the cyanobacterium Synechococcus PCC7942 were inoculated alone and in mixed culture in a ratio of 10:1 with and without flurochloridone. Aliquots were removed daily and counted under the microscope. 8A represents the Chlamydomonas pds transformants counts and 8B represents the cyanobacterium Synechococcus PCC7942 counts.

Figure 9:
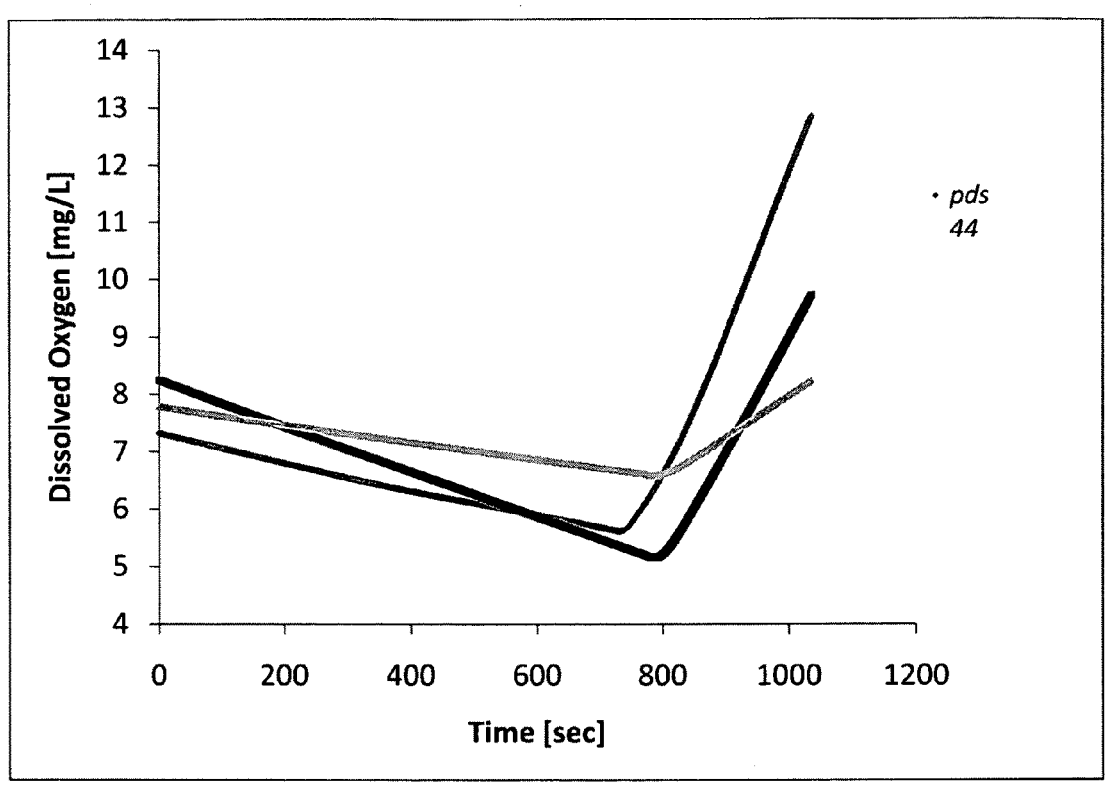

FIG. 9. Oxygen evolution curves of Chlamydomonas reinhardtii (WT) and pds (pdsI38, pds I44) transformants under 1000 µmol photons $m^{-2}$ $s^{-1}$. Dark incubation for approximately 12 min was applied, followed by ~8 min of illumination. Rates of dark oxygen consumption and net oxygen evolution were calculated and compared.

Figure 10A:
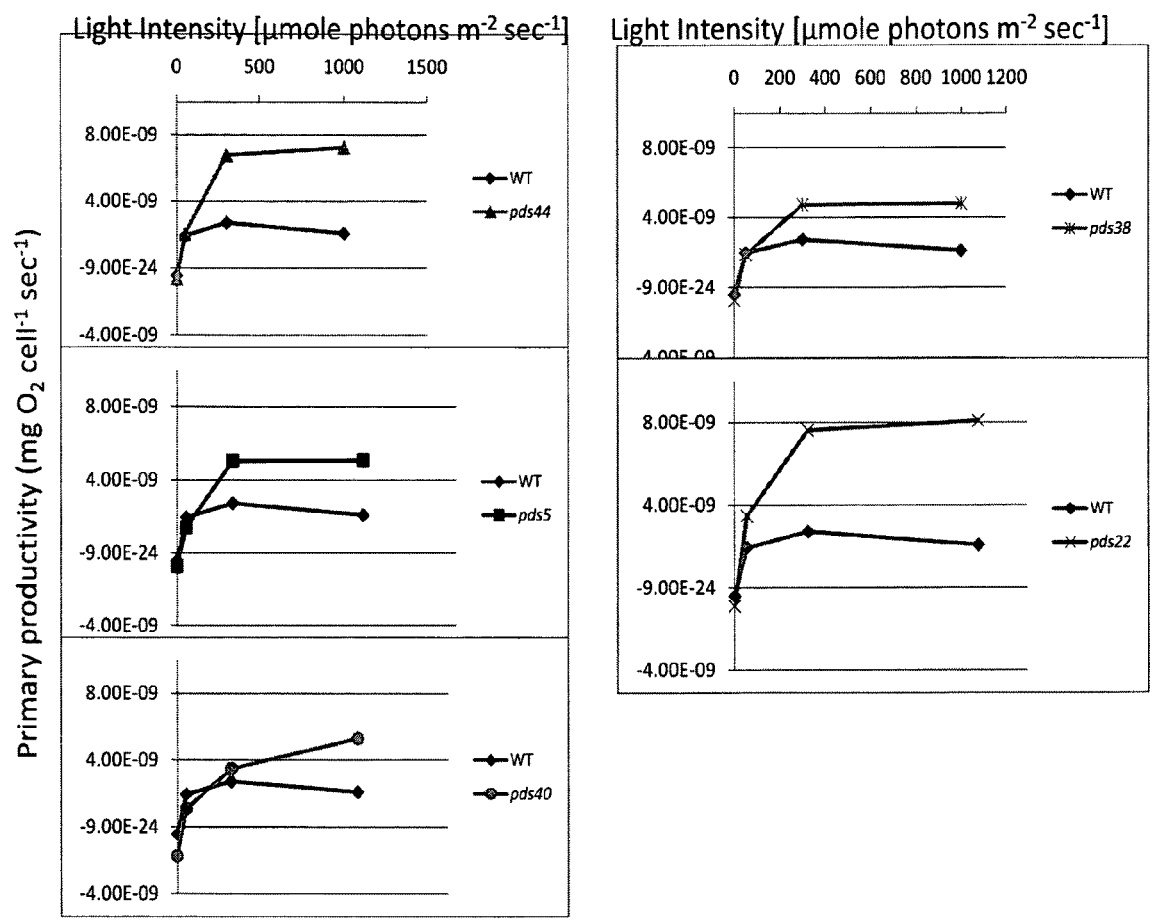
Figure 10B:
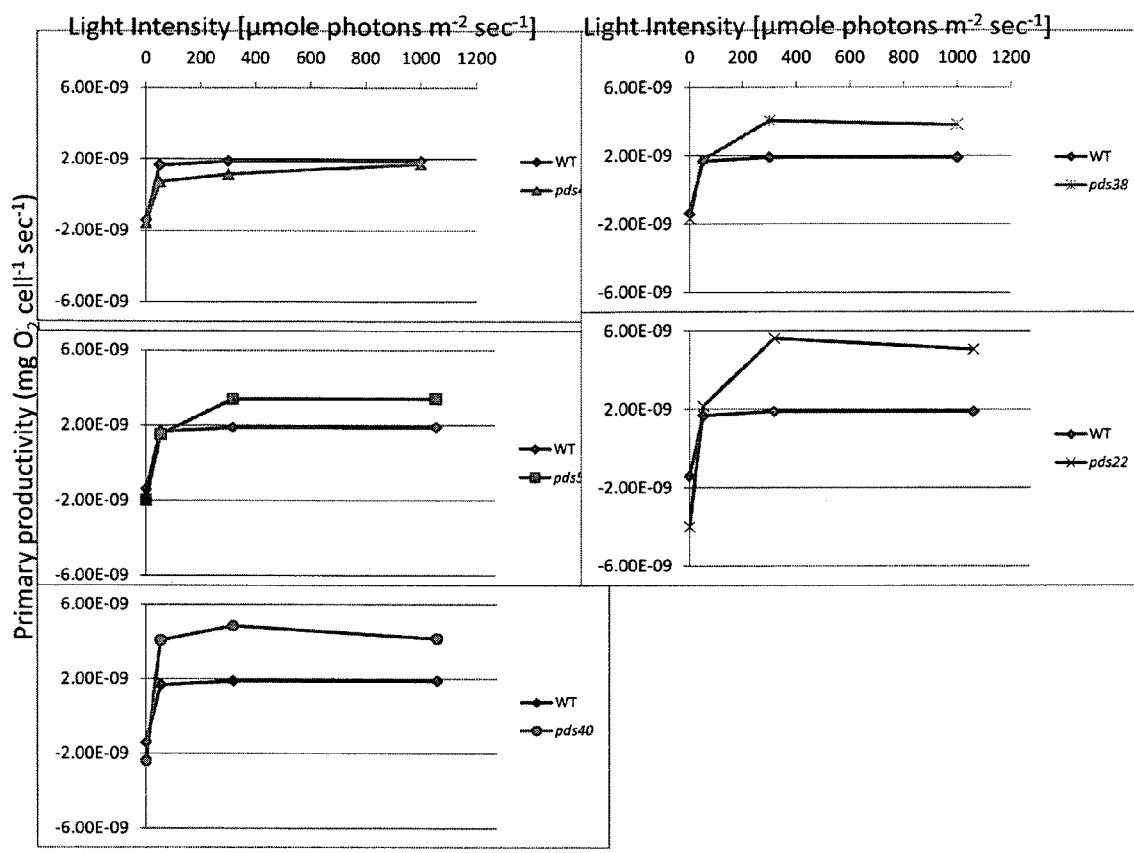

FIG. 10 Enhanced photosynthesis of Chlamydomonas reinhardtii pds transformants (pdsII5; pds I44; pds II22; pds I38; pds I40) versus wild-type (WT). Incubations lasted approximately 10 minutes. A and B represent two different experiments conducted with the same strains.

Figure 11A:
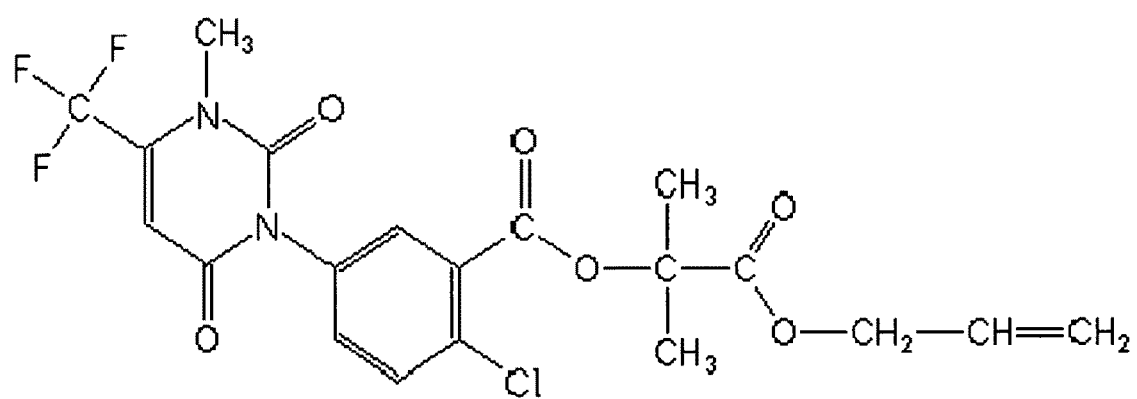
Figure 11B:
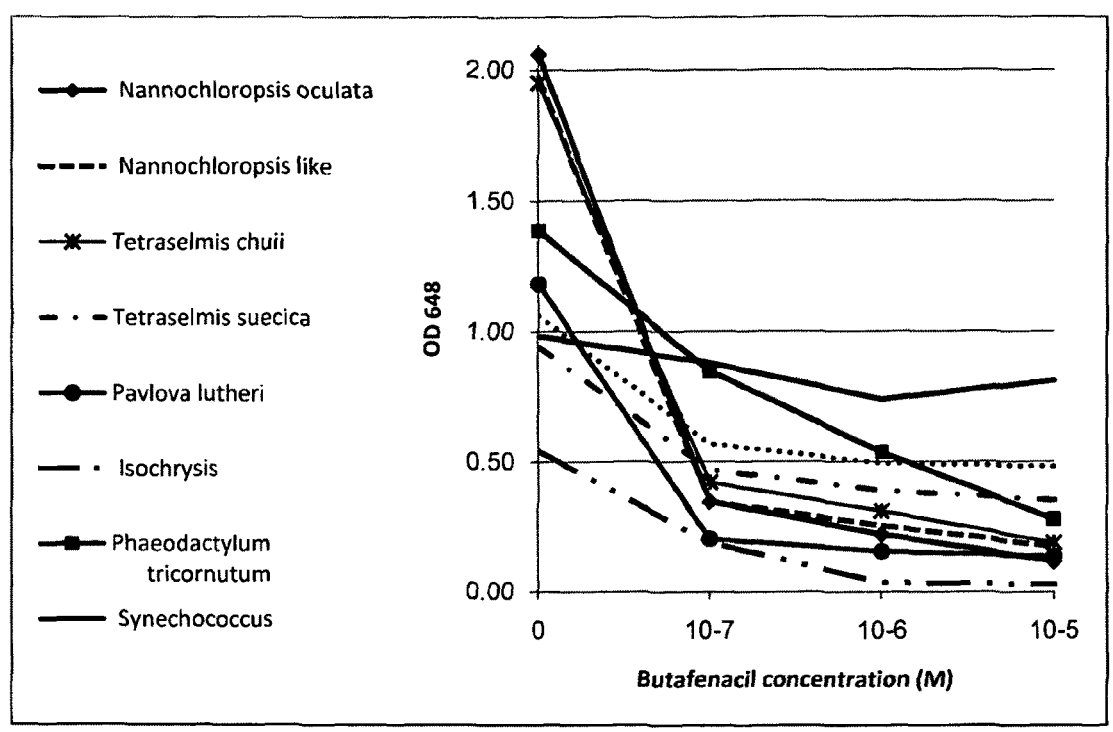

FIG. 11 A Chemical structure of butafenacil. B. Butafenacil dose response on wild type algae and cyanobacteria. Strains were cultured at $OD_{648}$=0.1 in 24 well plate and butafencil was applied at concentrations of $10^{-5,6,7}$M. After a week $OD_{648}$ of the cultures was measured.

DETAILED DESCRIPTION OF THE INVENTION

The present invention provides genetically modified algae and cyanobacteria that are resistant to one or more herbicides, whereby the transgenic strains can be cultivated in axenic monoculture by controlling unwanted species with herbicide applications. The present invention further provides a method to limit the establishment of the transgenic strains in natural ecosystems through their impaired photosynthetic activity in naturally occurring light conditions.

Moreover, the present invention provides a method to cultivate the transgenic algae and/or cyanobacteria in monoculture by controlling unwanted species with herbicides and prevent growth of zooplankton by use of high carbon dioxide concentrations.

In one embodiment the Hydrilla pds-gene (Michel et. al., 2004) was synthesized de novo according to the appropriate codon usage of the desired algae/cyanobacteria. The de novo synthesized herbicide resistant pds gene is then cloned for algae under the control of rbcS2 and or fcpA/35S/ubiquitin/tubulin promoters and 3'rbcS2/fcpA/fcpB terminators, in the plasmids pSI103 and or pPHAT1 (Sizova et. al 2001; Lioudmila, et. al 2000) and for cyanobacteria under the constitutive promoter of the rbcLS operon (Deng and Coleman 1999) in the plasmid pCB4 as well as into various expression vectors, allowing various levels of expressions driven by different promoters, including constitutive, inducible and log phase temporal promoters. The pds transformants are selected for the highest levels of the appropriate herbicide resistances with the least effects on growth in special situations.

In another embodiment the Amaranthus tuberculatus ppo-gene (Patzoldt et. al., 2006) was synthesized de novo according to the appropriate codon usage of the desired algae/cyanobacteria. The de novo synthesized herbicide resistant ppo gene is then cloned for algae under the control of rbcS2 and or fcpA/35S/ubiquitin/tubulin promoters and 3'rbcS2/fcpA/fcpB terminators, in the plasmids pSI103 and or pPHAT1 (Sizova et. al 2001; Lioudmila, et. al 2000) and for cyanobacteria under the constitutive promoter of the rbcLS operon (Deng and Coleman 1999) in the plasmid pCB4 as well as into various expression vectors, allowing various levels of expressions driven by different promoters, including constitutive, inducible and log phase temporal promoters.

According to yet another embodiment, the pds gene is used as selectable marker with phytoene desaturase inhibiting herbicides.

According to still another embodiment the pds gene is used as a selectable marker with phytoene desaturase herbicides for co-transformations with other genes needed in the algae such as reduced RUBISCO, reduced antennae size, enhanced fluorescence proteins, reduced or enhanced starch or other products, deletion or formation or modified or enhanced lipid biosynthesis, or any other gene that may be desirable in the algae or cyanobacteria. The herbicide resistant gene is either co-transformed with other genes such as genes encoding modified protein and starch synthesis, reduced RUBISCO, reduced antenna size or modified lipid or protein biosynthesis or the genes are constructed together on the same plasmid and are transformed to the desired algae and cyanobacteria. New genes can also be introduced in the background of transgenic algae that were transformed with the mentioned genes According to yet another embodiment the, ppo gene is used as a selectable marker with protoporphyrinogen oxidase inhibiting herbicides.

According to a further embodiment the ppo gene is used as a selectable marker with protoporphyrinogen oxidase inhibiting herbicides for co-transformations with other genes needed in the algae such as reduced RUBISCO, reduced antennae size, enhanced fluorescence proteins, reduced or enhanced starch or other products, deletion or formation or modified or enhanced lipid biosynthesis, or any other gene that may be desirable in the algae or cyanobacteria. The herbicide resistant gene is either co-transformed with other genes such as genes encoding modified protein and starch synthesis, reduced RUBISCO, reduced antenna size or modified lipid or protein biosynthesis or the genes are constructed together on the same plasmid and are transformed to the desired algae and cyanobacteria. New genes can also be introduced in the background of transgenic algae that were transformed with the mentioned genes.

According to one embodiment of this invention, cultivated algae and cyanobacteria species were rendered resistant to flurochloridone/fluridone by transformation with a resistant type phytoene desaturase (pds) gene under a constitutive promoter. Application of the herbicides flurochloridone/fluridone to the transgenic cultured algae and cyanobacteria results in establishment of the desired algae and cyanobacteria without contamination by other algae and cyanobacteria, because they are killed by fluridone/flurochioridone. Under a preferred embodiment flurochloridone is preferable to fluridone, as lower concentrations could be used.

According to yet another embodiment of this invention, cultivated algae and cyanobacteria species were rendered resistant to butafenacil or flumioxazin by transformation with resistant protoporphyrinogen oxidase (ppo) gene under a constitutive promoter. Application of the herbicide butafenacil or flumioxazin to the transgenic cultured algae and cyanobacteria results in establishment of the desired algae and cyanoacteria without contamination by other algae and cyanobacteria, because they are killed by butafenacil or flumioxazin.

The invention is now described by non-limiting examples. One of ordinary skill in the art would realize that various modifications can be made without departing from the spirit of the invention. The examples below show that the process according to this invention is useful, novel, non obvious and it greatly simplifies the harvest and processing of microalgae and cyanobacteria.

In the various embodiments, algae and cyanobacteria were chosen from the following organisms: *Phaeodactylum tricornutum, Amphiprora hyaline, Amphora* spp., *Chaetoceros muelleri, Navicula saprophila, Nitzschia* sp., *Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus PCC6301, Botryococcus braunii, Gloeobacter violaceus PCC7421, Synechococcus PCC7002, Synechococcus PCC7942, Synechocystis PCC6803, Thermosynechococcus elongatus BP-1, Nannochloropsis oculata, Nannochloropsis salina, Nannochloropsis* spp., *Nannochloropsis gaditana, Isochrysis galbana, Aphanocapsa* sp., *Botryococcus sudeticus, Nannochloris* spp., *Pavlova* spp., *Euglena gracilis, Neochloris oleoabundans, Nitzschia palea, Pleurochrysis carterae, Tetraselmis chuii, Nannochloris* spp. It is however, clear for one skilled in the art that this list is not exclusive, but that various other genera and species can be used as well.

EXAMPLE 1

Synthesis of Appropriate Flurochloridone and Fluridone-Resistant Phytoene Desaturase Genes The pds gene was de novo synthesized according to the appropriate codon usage of the desired algae and the desired cyanobacteria or according to general algae and general cyanobacterial codon usage. The synthetic genes harbor the histidine, cysteine or serine amino acid, corresponding to arginine$_{304}$histidine in *Hydrilla*.

The phytoene desaturase gene harboring the histidine mutation (SEQ ID NO:1) was custom synthesized according to the *Chlamydomonas* codon usage by the GENEART AG, Regensburg, Germany (http://www.geneart.com). The gene was synthesized with a BstBI restriction site on the 5' and BamHI on the 3' for direct cloning into pSI103 algae expression vector. The cloning was conducted with algae originating from a large taxonomical cross section of species (Table 1). The algae included: *Chlamydomonas reinhardtii, Pavlova lutheri, Isochrysis* sp. CS-177, *Nannochloropsis oculata* CS-179, *Nannochloropsis like* CS-246, *Nannochloropsis salina* CS-190, *Tetraselmis suecica, Tetraselmis chuii* and *Nannochloris* sp. as representatives of all algae species.

TABLE 1

| Phylogeny of some of algae used | | | | |
|---|---|---|---|---|
| Genus | Family | Order | Phylum | Sub-Kingdom |
| Chlamydomonas | Chlamydomonadaceae | Volvocales | Chlorophyta | Viridaeplantae |
| Nannochloris | Coccomyxaceae | Chlorococcales | Chlorophyta | Viridaeplantae |
| Tetraselmis | Chlorodendraceae | Chlorodendrales | Chlorophyta | Viridaeplantae |
| Phaeodactylum | Phaeodactylaceae | Naviculales | Bacillariophyta | Chromobiota |
| Nannochloropsis | Monodopsidaceae | Eustigmatales | Heterokontophyta | Chromobiota |
| Pavlova | Pavlovaceae | Pavlovales | Haptophyta | Chromobiota |
| Isochrysis | Isochrysidaceae | Isochrysidales | Haptophyta | Chromobiota |

Phylogeny according to: http://www.algaebase.org/browse/taxonomy/

Note: Many genes that in higher plants and Chlorophyta are encoded in the nucleus are encoded on the chloroplast genome (plastome) in the Chromobiota, red lineage algae (Grzebyk et al., 2003).

The *Hydrilla* phytoene desaturase gene is customized with the histidine mutation according to the codon usage of cyanobacterium *Synechococcus* PCC7002 (SEQ ID NO:2) and the cloning is conducted with the following cyanobacterial species: *Synechococcus* PCC7002, *Synechococcus* WH-7803, *Thermosynechococcus elongatus* BP-1.

Resistance to phytoene desaturase inhibiting herbicides is also conferred by transformation with *Hydrilla* phytoene desaturase with the serine mutation according to the codon usage of *Chlamydomonas* (SEQ ID NO:3), *Hydrilla* phytoene desaturase with the serine mutation according to the codon usage of the cyanobacterium *Synechococcus* PCC7002 (SEQ ID NO:4), *Hydrilla* phytoene desaturase with the cysteine mutation according to the codon usage of *Chlamydomonas* (SEQ ID NO:5), and *Hydrilla* phytoene desaturase with the cysteine mutation according to the codon usage of the cyanobacterium *Synechococcus* PCC7002 (SEQ ID NO:6).

EXAMPLE 2

Cloning the Resistant Phytoene Desaturase into an Expression Vector

The de novo synthesized pds gene SEQ ID NO:1 was cloned under the control of rbcS2 and or fcpA/35S/ubiquitin/tubulin promoters and 3'rbcS2/fcpA/fcpB terminators, in the plasmids pSI103 and or pPHAT1 (Sizova et al., 2001; Zaslayskaia et al., 2000). For cyanobacteria, the gene (SEQ ID NO:2) is cloned under the constitutive promoter of the rbcLS operon (Deng and Coleman 1999) in the plasmid pCB4 as well as into various expression vectors, allowing various levels of expressions driven by different promoters, including constitutive, inducible and log phase temporal promoters.

The synthetic pds gene with the histidine mutation was cloned using BamHI, BstBI restriction sites into the pSI103 expression vector under the control of rbcS2 promoter (FIG. 1; pSI103-PDS).

The synthetic pds gene was also cloned under the fcpA promoter in pPhaT1 by blunt ligation. The pds was digested from pSI103 by BamHI and BstBI, the pPhaT1 was digested by BamHI followed by filling in and blunt ligation (FIG. 1: pPhaT-PDS).

The synthetic pds gene was also cloned under the cauliflower mosaic virus (CaMV) 35s and 35S omega promoters in pPhaT1 by BamHI and EcoRI and replaced the fcpA promoter (FIG. 1: pPhaT1-35S-PDS).

The synthetic pds gene was also cloned under the ubiquitin promoter in the pSI103 expression vector. The maize ubiquitin promoter accession no. AY342393 was excised from the pUB-AG vector by XbaI and replaced the Rbsc-Hsp70 promoters in pSI103 which was excised by XbaI, BstBI, followed by filling in and blunt ligation (FIG. 1: pSI103-Ubiq-PDS).

The synthetic pds gene was further cloned under the tubulin promoter (XM_001693945) in the pSI103 expression vector. The tubulin promoter was excised from the pKS-aph7"-lox vector by SacI, EcoRI and replaced the hsp70-rbsC-promoters in pSI103 by digestion with NotI, BstBI followed by filling in and blunt ligation (FIG. 1: pSI103-Tub-PDS).

The synthetic pds gene was also cloned under the actin promoter in the pSI103 expression vector. The rice actin promoter (accession no. EU155408) was excised from the pUB-AG vector by HindIII, SmaI and replaced the hsp70-rbsC promoters in pSI103 which was excised by XbaI, BstBI followed by filling in and blunt ligation (FIG. 1: pSI103-Act-PDS).

EXAMPLE 3

Transformation of the Resistant Phytoene Desaturase into Algae and Cyanobacteria Algae and cyanobacteria were transformed with the resistant form of phytoene desaturase gene by various methods described below. Importantly, this is the first time microporation transformation method is described and applied to transformation of algal or cyanobacterial cells.

I. Electroporation

Fresh algal cultures were grown to mid exponential phase ($2-5*10^6$ cells/ml) in artificial sea water (ASW)+F/2 media. Cells were then harvested and washed twice with fresh media. After re-suspending the cells in 1/50 of the original volume, protoplasts were prepared by adding an equal volume of 4% hemicellulase (Sigma) and 2% Driselase (Sigma) in ASW and were incubated at 37° C. for 4 hours. Protoplast formation was tested as a lack of Calcofluor white (Fluka) staining of cell walls. Protoplasts were washed twice with ASW containing 0.6M D-mannitol and 0.6M D-sorbitol and re-suspended in the same media, after which DNA was added (10 µg linear DNA for each 100 µl protoplasts). Protoplasts were transferred to cold electroporation cuvettes and incubated on ice for 7 minutes then pulsed by the ECM 830 electroporator (BTX Instrument Division, Harvard Apparatus, Inc., Holliston, Mass., USA). A variety of pulses were usually applied, ranging from 1000 to 1500 volts, 10-20 ms each pulse. Each cuvette was pulsed 5-10 times. Immediately after pulsing the cuvettes were placed on ice for 5 minutes and then the protoplasts were added to 250 µl of fresh growth media (without selection). After incubating the protoplasts for 24 hours in low light, the cells were plated onto selective solid media and incubated under normal growth conditions until single colonies appeared.

II. Microporation

Fresh algal cultures were grown to mid exponential phase ($2-5*10^6$ cells/ml) in ASW+F/2 media. A 10 ml sample of each culture was harvested, washed twice with DPBS (Dulbecco's phosphate buffered saline, Gibco) and resuspended in 250 µl of buffer R (supplied by Digital Bio, NanoEnTek Inc., Seoul, Korea, microporation apparatus and kit). After adding 8 µg linear DNA to every 100 µl cells, the cells were pulsed. A variety of pulses was usually needed, depending on the type of cells, ranging from 700 to 1700 volts, 10-40 ms pulse length; each sample was pulsed 1-5 times. Immediately after pulsing, the cells were transferred to 200 µl fresh growth media (without selection). After incubating for 24 hours in low light, the cells were plated onto selective solid media and incubated under normal growth conditions until single colonies appeared.

III. Particle Bombardment

Fresh algal culture were grown to mid exponential phase ($2-5*10^6$ cells/ml) in ASW+F/2 media. 24 hours prior to bombardment cells were harvested, washed twice with fresh ASW+F/2 and resuspended in 1/10 of the original cell volume in ASW+F/2. 0.5 ml of the cell suspension is spotted onto the center of a 55 mm Petri dish containing solidified ASW+F/2 media. Plates are left to dry under normal growth conditions. Bombardment was carried out using a PDS 1000/He biolistic transformation system according to the manufacturer's (BioRad Laboratories Inc., Hercules, Calif., USA) instructions using M10 tungsten powder (BioRad Laboratories Inc.) for cells larger than 2 microns in diameter, and tungsten powder comprised of particles smaller than 0.6 microns (FW06, Canada Fujian Jinxin Powder Metallurgy Co., Markham, ON, Canada) for smaller cells. The tungsten was coated with linear DNA. 1100 or 1350 psi rupture discs were used. All disposables were purchased from BioRad Laboratories Inc., (Hercules, Calif., USA). After bombardment the plates were incubated under normal growth conditions for 24 hours after which the cells were plated onto selective solid media and incubated under normal growth conditions until single colonies appeared.

IV. Glass Beads

Cells ($4 \times 10^7$) in 0.4 ml of growth medium containing 5% PEG6000 were transformed with DNA ($1 \pm 5$ mg) by the glass bead vortexing method (Kindle, 1990). The transformation mixture was then transferred to 10 ml of nonselective growth medium for recovery. The cells were kept for at least 18 h at 25° C. in the light. Cells were collected by centrifugation and plated at a density of $13 \times 10^7$ cells per 80 mm plate. Transformants were selected on fresh SGII ((http://www.chlamy.org/SG.html) agar plates containing $3 \times 10^{-7}$M flurochloridone.

The above described procedures were carried out on the following algae: *Chlamydomonas reinhardtii, Pavlova lutheri, Isochrysis* sp. CS-177, *Nannochloropsis oculata* CS-179, *Nannochloropsis like* CS-246, *Nannochloropsis salina, Tetraselmis suecica, Tetraselmis chuii*, and *Nannocloropsis* sp. as representatives of all algae species Cyanobacterial species *Synechococcus* PCC7002, *Synechococcus* WH-7803, *Thermosynechococcus elongatus* BP-1 were used as representatives of all cyanobacterial species using a standard protocol as set out in (Golden, et al. 1987). Briefly, cells are harvested by centrifugation and resuspended in fresh growth medium (ASW+F/2 for *Synechococcus* PCC7002 and *Synechococcus* WH-7803; and BG-11 for *Thermosynechococcus elongatus* BP-1) at a concentration of $2\text{-}5 \times 10^8$ cells/ml. To one ml of this cell solution the appropriate plasmid construct is added to a final concentration of 2-5 µg/ml. Cells were incubated in the dark for 8 hours followed by a 16 h light incubation prior to plating on fresh media plates containing flurochloridone or fluridone to select for the colonies that grow at the highest rates without affecting algal growth. Plates are incubated under growth conditions adjusted to the preferences of each strain. Flurochloridone or fluridone resistant colonies were visible after 7-10 days. This is modified for each organism according to its needs, based on modifications of standard protocols.

Figure 1:
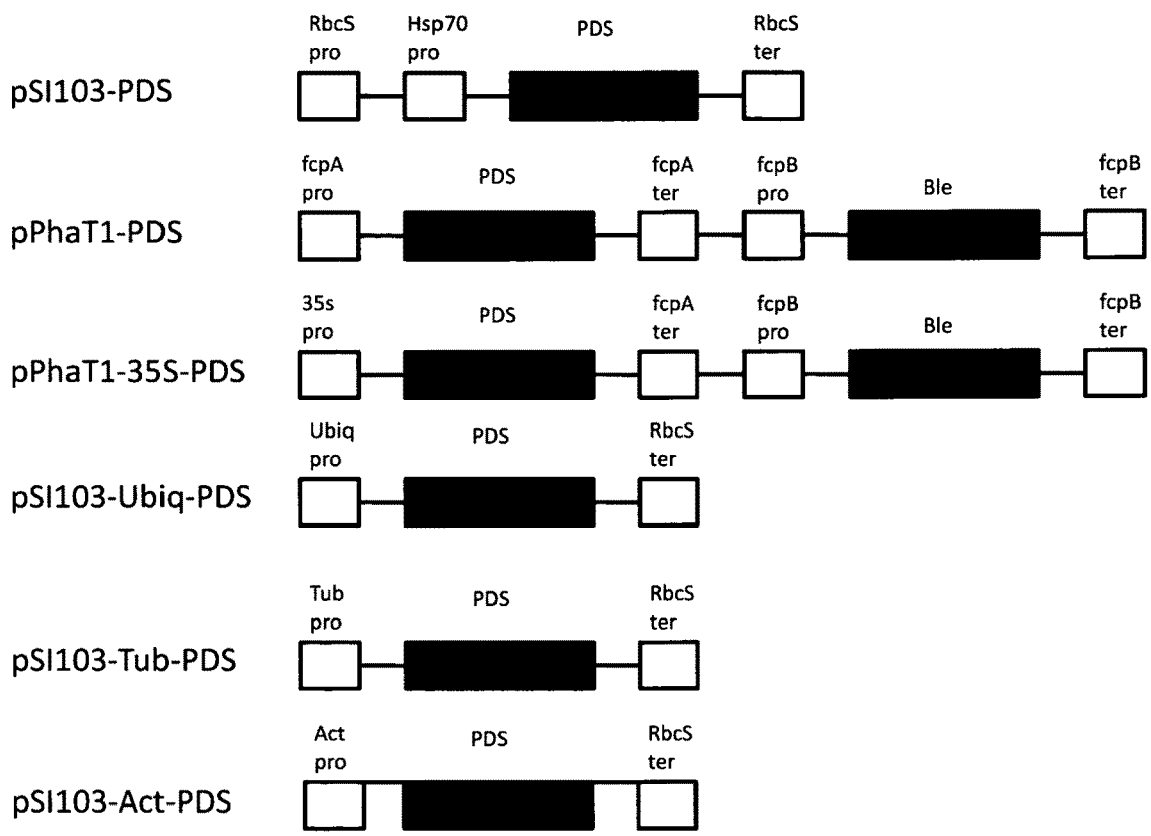
FIG. 1. Schematic illustration of the constructs of the synthetic pds gene (SEQ ID NO:1) under various promoters in various expression vectors as used in this disclosure.
Figure 2:
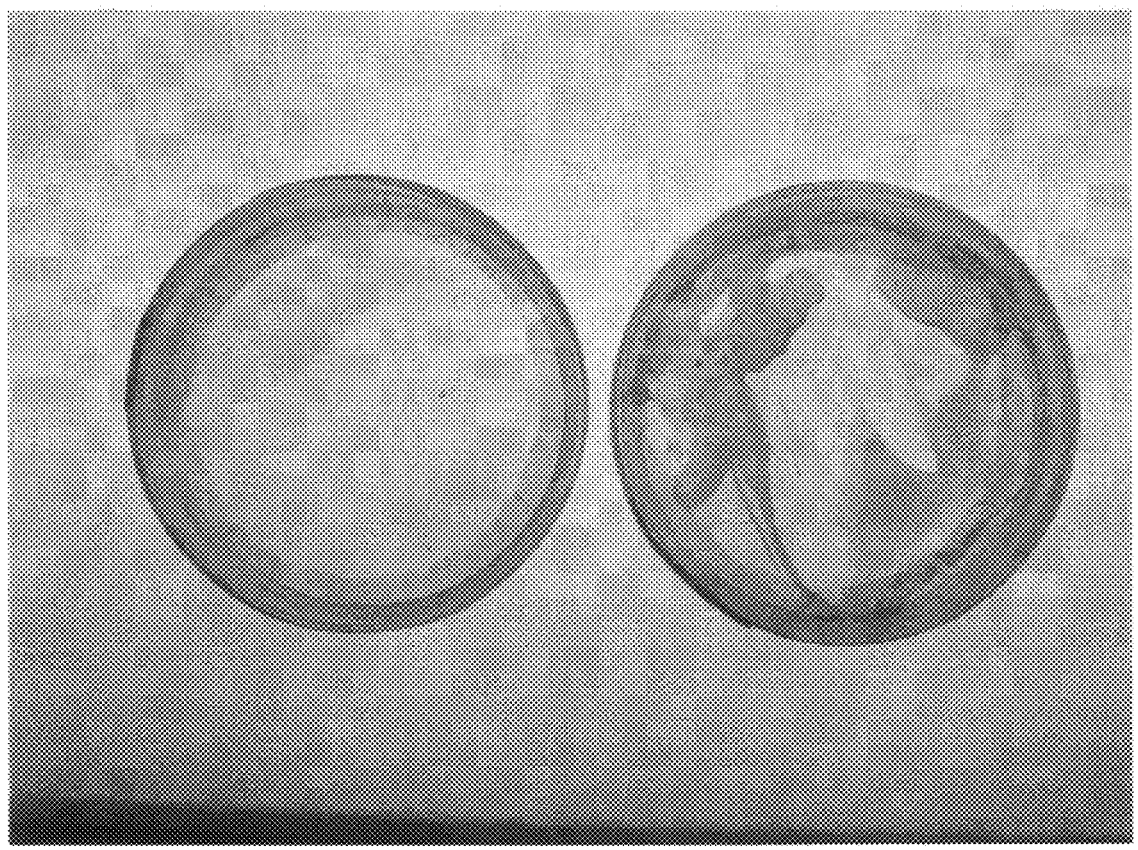
FIG. 2. Chlamydomonas cells were transformed with the synthetic pds (SEQ ID NO:1) gene harboring the histidine mutation (right panel) as well as control cells that were not transformed with DNA (left panel) and plated on SGII medium containing $10^{-7}$M flurochloridone. Growth of transformants was visible within two weeks. 100 of the clones were picked for further studies.

*Chlamydomonas* cells were transformed with the pSI103-PDS construct, harboring the histidine mutation (corresponding to *Hydrilla* Arg 304), using the glass beads transformation technique as described above and plated on SGII medium+ $10^{-7}$ M flurochloridone as is shown in FIG. 2.

Figure 3:
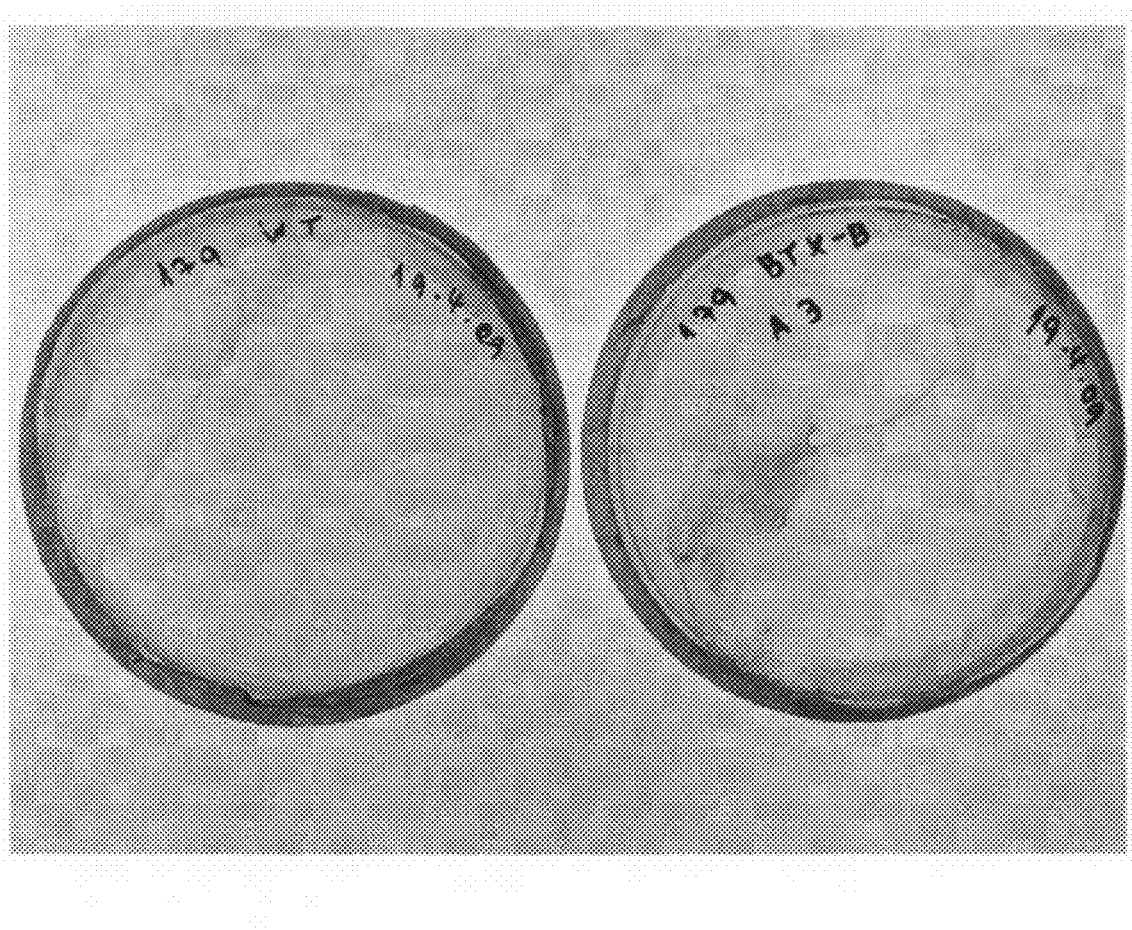
FIG. 3. Nannochloropsis cells were transformed with the pSI103-PDS construct (right panel) as well as control cells which were not transformed with DNA (left panel) plated on artificial sea water (ASW)+1 µM flurochloridone. The resistant material is also cross resistant to the phytoene desaturase inhibitors fluridone, picolinafen, and norflurazon.

*Nannochloropsis oculata* CS179 cells were transformed with the PSI103-PDS construct using the ECM 830 electroporator (BTX Instrument Division, Harvard Apparatus, Inc., Holliston, Mass., USA) as described above. After transformation algae were plated on ASW+F/2 media (http://www.marine.csiro.au/microalgae/methods/) containing $10^{-7}$M flurochloridone. After two weeks, algal colonies both from the transformation and the mock were replated on ASW+ $10^{-6}$M flurochloridone plates. This allowed differentiation between false positives and true resistant clones (FIG. 3). This material was used in Example 4.

*Isochrysis galbana* was transformed by the particle bombardment technique (M10 tungsten powder, 1100 psi rupture discs). After two weeks, algal colonies from both the transformation and the mock were replated on ASW+$10^{-7}$ M flurochloridone plates. This allowed differentiation between false positives and true resistant clone. 10 stable resistant clones were isolated from the experiments by particle bombardment

EXAMPLE 4

Figure 4:
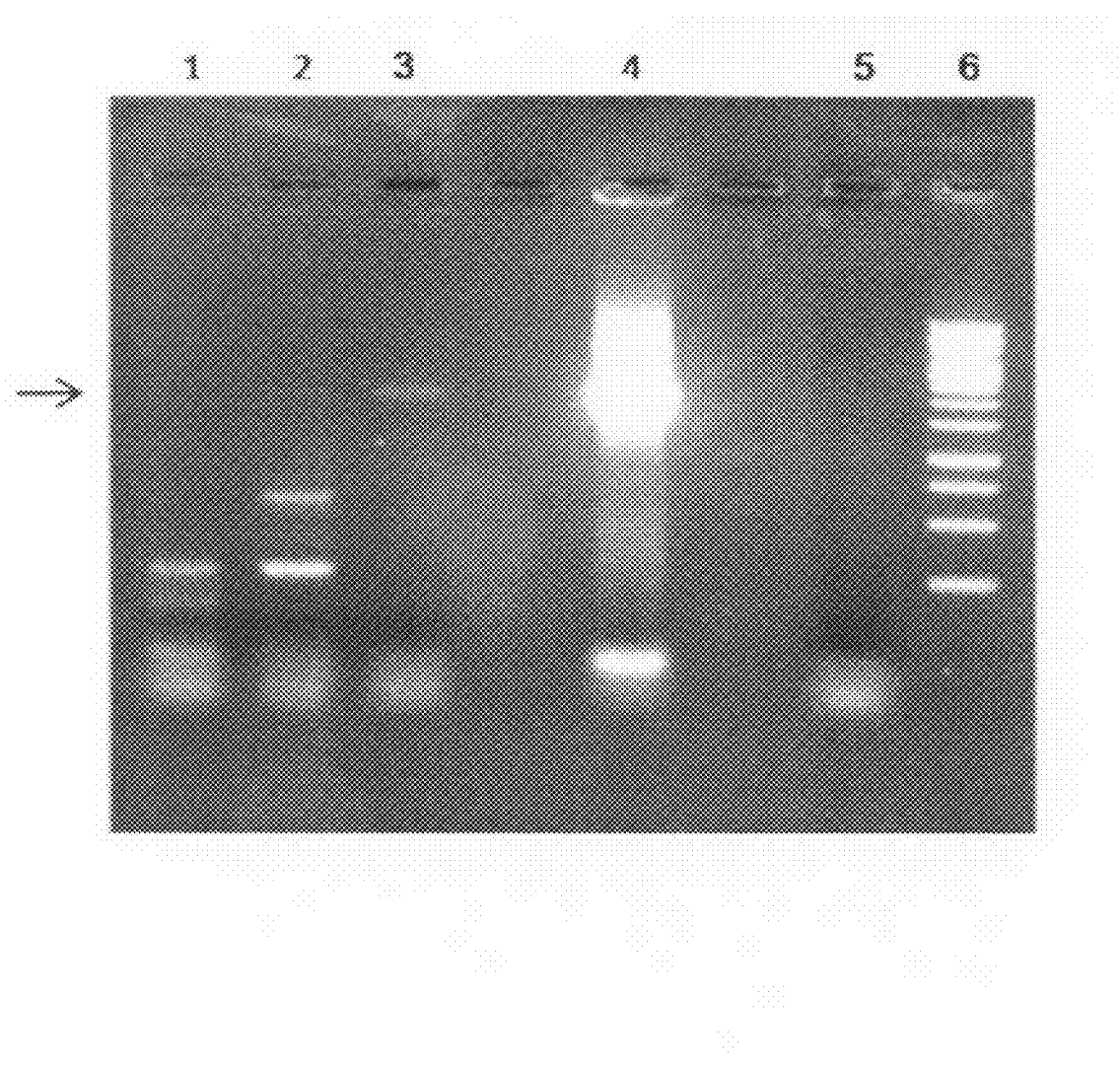
FIG. 4. PCR analysis to the Chlamydomonas bulk transformants with pSI103-PDS showing the insertion of the pds gene into the transformants (denoted by arrow). The numbers represent the following: wild type (1), transformed 1 (2), transformed 2 (3), positive control (the transformed plasmid) (4), no template DNA (5), molecular weight markers (6). More explanations are provided in the examples below.

Verification of the Presence of the Synthetic pds Gene Transformed Algae and Cyanobacteria Harboring the Resistant Phytoene Desaturase The transformants described in Example 3 were replated on fresh agar medium containing either $10^{-7}$M (*Chlamydomonas* and *Isochrysis*) or $10^{-6}$M (*Nannochloropsis*) of flurochloridone and cells were allowed to generate to visible colonies. After incubation for a week the most resistant colonies were chosen. To ascertain gene transformation PCR analysis was performed on wild type and flurochloridone resistant transformants (FIG. 4).

*Chlamydomonas* genomic DNA was extracted according to the following protocol: An algal pellet of approximately 5-10 µL in size was resuspended in 50 µL of 10 mM NaEDTA by vortexing, followed by incubation at 100° C. for 5 minutes and mixing by vortex. Cells were centrifuged at 12000 g for 1 minute and resuspended in double distilled water (DDW).

Polymerase chain reaction (PCR) analysis was performed on genomic DNA of wild type and flurochloridone resistant *Chlamydomonas* colonies using the following primers:

```
pSI103-1362:  AATGCAAGCAGTTCGCATGC   (SEQ ID NO: 7)

PDS reverse:  GGCGATGGTCAGGGTCTG     (SEQ ID NO: 8)
```

The PCR reaction medium was as follows: Genomic DNA 2 l, primer PDS reverse 1 µl, primer pSI103-1362 1 µl, 12.5 µl PCR mix (RedTaq, Sigma), 8.5 µl DDW and the program set at 94° C. for 5', and then 35 cycles of 94° C. for 1', 62° C. for 1', 72° C. for 2.5'. The PCR samples were separated on 1% agarose gel and viewed under UV light (FIG. 4).

Figure 5:
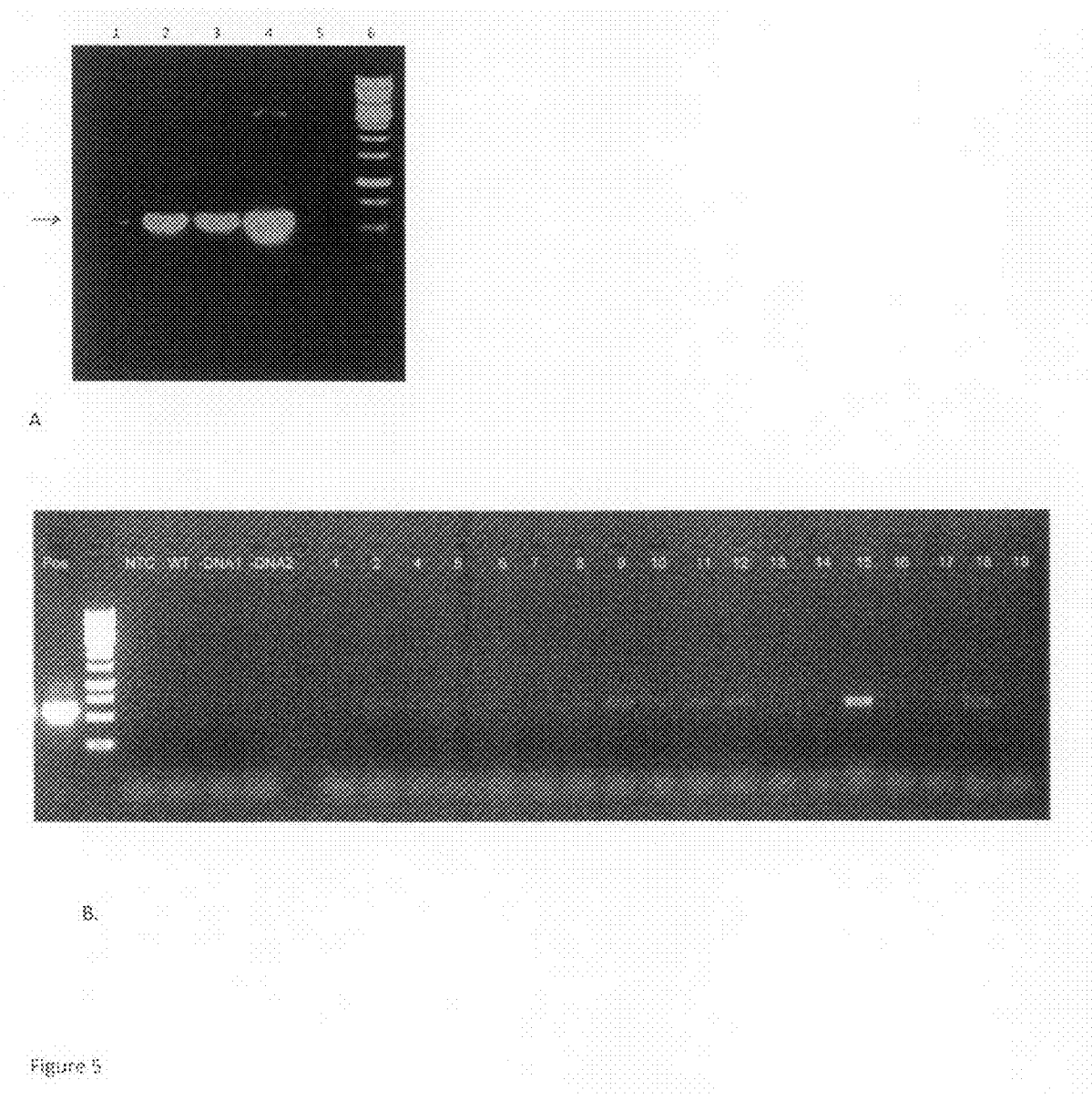
FIG. 5. PCR analysis of the Nannochloropsis oculata cells that were transformed with pSI103-PDS showing the insertion of the pds gene into the transformants (denoted by arrow).

PCR analysis was performed on genomic DNA of wild type and flurochloridone resistant *Nannochloropsis* colonies (FIG. 5) with the following primers:

```
PDS F short:  CGTGGTGGCCGTGAACCTGA   (SEQ ID NO: 9)

PDS R short:  CGCTGTTGCGGAAGCTGGAG   (SEQ ID NO: 10)
```

PCR content and program was set as follows: Genomic DNA 2 µl, primer PDS F short 1 µl, primer PDS R short 1 µl, 12.5 µl PCR mix (Sigma), 8.5 µl DDW. 94° C. 5', and then 35 cycles of 94° C. 30", 69° C. 30", 72° C. 30", PCR samples were separated on 1% agarose gel and viewed under UV light (FIG. 5A) Similarly, the same construct was incorporated into *Nannocloropsis* CS179 by microporation (FIG. 5B).

A dose response experiment was generated for the wild type *Chlamydomonas* and for its transformants. The wild types and the transformed algae were plated in SGII medium in 24 well plates with increasing concentrations of flurochloridone of 0.1 µM, 0.3 µM, 0.5 µM. Algae were plated without the herbicide as well as a control (FIG. 6). The most resistant colonies were chosen for further analysis.

EXAMPLE 5

Prevention of Algae and/or Cyanobacteria Contaminants

Figure 8B:
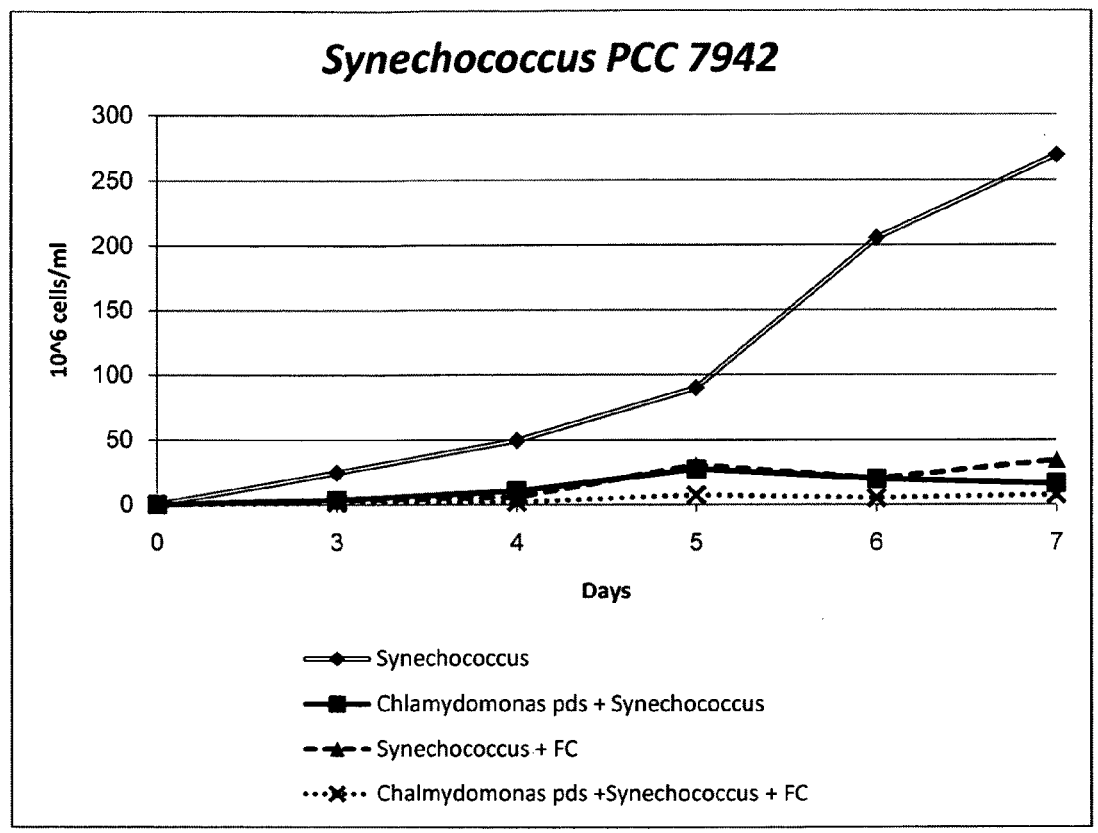

To address the question of contaminants, the *Chlamydomonas* pds transformants were mixed with the cyanobacterium *Synechococcus* PCC7942, which is known to overtake ponds. A *Chlamydomonas* pds transformant and the cyanobacterium *Synechococcus* PCC7942 were inoculated alone and in mixed cultures with and without flurochloridone. An example of a mixed culture is shown in FIG. 7. The mixed culture was inoculated in a ratio of 10:1 *Chlamydomonas* pds transformants: *Synechococcus* PCC7942 wild type, respectively. The cells were allowed to grow for one week in liquid medium, with daily removal of aliquots. Contaminants versus target *Chlamydomonas*-cells were counted under the microscope (FIG. 8). While the growth of the resistant pds *Chlamydomonas* cells was unaffected by the flurochloridone addition (FIG. 8A), the growth of *Synechococcus* PCC7942 cells was completely inhibited, implying that this potential contaminant is not able to outcompete the resistant *Chlamydomonas* culture.

EXAMPLE 6

Prevention of Contaminants by the Use of Slow Released Herbicide, Embedded in the Plastic/Polyethylene of the Photobioreactor A hydrophobic herbicide/biocide such as flurochloridone or fluridone and/or butafenacil flumioxazin is/are applied using a volatile organic solvent such as xylene on the inner side of the polyethylene algae photobioreactor or pond liner, such that if it were fully released into the subsequent growth medium the concentration would reach a final concentration of $10^{-5}$ to $10^{-7}$M. Transgenically resistant algae or cyanobacteria versus wild-type are inoculated in the treated photobioreactors after the solvent has evaporated. In commercial production, the herbicides can be added during production of the polyethyelene.

Culture aliquots are removed daily and cell densities of wild types and the transformed algae or cyanobacteria are compared. While the growth of the resistant pds transformed algae is unaffected by the addition of flurochloridone or fluridone and/or butafenacil or flumioxazin, the growth of the wild type culture is completely inhibited, implying that the incorporation of herbicide into the bioreactor lining during plastic manufacture provides advantage to the herbicide resistant algae and cyanobacteria.

EXAMPLE 7

Greater Photosynthetic Efficiency of pds Transgenic Algae in Dense Cultures at High Intensites One of the important parameters indicating the welfare of a photoautotrophic culture is its photosynthetic efficiency. We used the following methodologies to show the photosynthetic activity: Oxygen evolution—using Clark Type electrodes. Variable fluorescence—using PAM (Pulse Amplitude Modulated Fluorometry) We also evaluate dark oxygen consumption, in order to estimate net photosynthetic potential of the algal culture. As part of the photosynthetic evaluation we follow several abiotic parameters that potentially influence the physiological state of the cultures.

Light intensity tolerance (at a given cell density) is evaluated. P/I (photosynthesis vs. irradiance) curves are used to determine optimal light intensity per cell.

Performance at different $CO_2$ levels (e.g. ambient; 1%; 5%; 14%-100%). This is coupled with pH tolerance.

Temperature tolerance. Each culture is tested to attain the optimal temperature. In addition, temperatures are raised to the highest point possible without inhibiting other culture activities.

Photosynthetic Activity: Oxygen Evolution

Measurements of $O_2$ concentrations were performed using a Clark type $O_2$ electrode (Pasco Scientific, Roseville, Calif.). Twenty mL of cell suspension corresponding to 15 μg chlorophyll/mL were placed in an $O_2$ electrode chamber, at relevant temperature (22° C.). Cells were exposed to various light intensities (i.e. 50, 300 and 1000 μmol photons $m^{-2} s^{-1}$). Dark incubations were performed in air-tight vessels to follow dark oxygen consumption.

We compared a wild type culture of *Chlamydomonas reinhardtii* with its pds transformants. Results are shown in FIG. 9, and indeed reveal that not only was the photosynthesis of the transformants not inhibited but they actually exhibited improved photosynthetic activity, implying an enhanced biomass production.

The overall outcome from the analyses shown in FIGS. 9 and 10 implies that the selected transformants are both resistant to the herbicide and they perform better than wild type in terms of oxygen evolution. Taken together, these transgenic cultures are relevant candidates to be grown at large scale production systems as well as being used as a platform for future transformations.

Fluorescence Measurements

Electron transfer activity of photosystem II is measured by pulse modulated fluorescence (PAM) kinetics using PAM-101 (Walz, Effertlich, Germany). Light intensity (measured at the surface of the chamber) of the modulated measuring beam (at 1.6 kHz frequency) is 0.1 μmol photons $m^{-2} s^{-1}$. White actinic light is delivered by a projector lamp at 50-1500 μmol photons $m^{-2} s^{-1}$ as required in different experiments and is used to assess steady state fluorescence ($F_s$). Maximum fluorescence ($F_m$) is measured with saturating white light pulses of 4000 μmol photons $m^{-2} s^{-1}$ for 1 s. At a worse case scenario, a normal electron transfer activity is expected from transformants in order to be considered as relevant for up-scaling. An improved activity may imply a culture that will perform better than the wild type. The advantage of the method is a quick analysis on a wide array of candidate transformants.

EXAMPLE 8

Synthesis of Appropriate Butafenacil and Protox Resistant Protoporphyrinogen Oxidase Gene The ppo gene was de novo synthesized according to the appropriate codon usage of the desired algae and the desired cyanobacteria or according to general algae and general cyanobacterial codon usage. The ppo gene with the glycine deletion at position 210 according to the *Amaranthus tuberculatus* GenBank accession no. DQ386116 (SEQ ID NO:11) was custom synthesized, according to the *Chlamydomonas* codon usage by the by the GENEART synthesis company (http://www.geneart.com/). The gene was synthesized with the BstBI,EcoRI restriction site on the 5' and BamHI on the 3' for direct cloning into pSI103 and pPhaT1 algae expression vectors. Transformation is conducted for the following algae: *Chlamydomonas reinhardtii, Pavlova lutheri, Isochrysis* CS-177, *Nannochloropsis oculata* CS-179, *Nannochloropsis like* CS-246, *Nannochloropsis salina* CS-190, *Tetraselmis suecica, Tetraselmis chuii* and *Nannochloris* sp. as representatives of all algae species (see Table 1).

*Amaranthus tuberculatus* protoporphyrinogen oxidase gene according to the codon usage of the cyanobacterium *Synechococcus* PCC7002 (SEQ ID NO:12) is transformed in cyanobacteria *Synechococcus* PCC7002, *Synechococcus* WH-7803, *Thermosynechococcus elongatus* BP-1 as representatives of all cyanobacterial species.

EXAMPLE 9

Cloning the Resistant Protoporphyrinogen Oxidase Gene into an Expression Vector

The de novo synthesized ppo gene is cloned under the control of rbcS2 and or fcpA/35S/ubiquitin/tubulin promoters and 3'rbcS2/fcpA/fcpB terminators, in the plasmids pSI103 and or pPHAT1 (Sizova et. al 2001; Zaslayskaia et. al 2000). For cyanobacteria it was cloned under the constitutive promoter of the rbcLS operon (Deng and Coleman 1999) in the plasmid pCB4 as well as into various expression vectors, allowing various levels of expressions driven by different promoters, including constitutive, inducible and log phase temporal promoters.

EXAMPLE 10

Transformation of the Resistant Protoporphyrinogen Oxidase Gene into Algae and Cyanobacteria Constructs are transformed using various techniques as described in Example 3. These procedures are carried out on the following algae: *Chlamydomonas reinhardtii, Pavlova lutheri, Isochrysis* CS-177, *Nannochloropsis oculata* CS-179, *Nannochloropsis like* CS-246, *Nannochloropsis salina, Tetraselmis suecica, Tetraselmis chuii, Nannochloris* sp. and as representatives of all algae species (Table 1).

Constructs are incorporated into the cyanobacteria *Synechococcus* PCC7002, *Synechococcus* WH-7803, *Thermosynechococcus elongatus* BP-1 as representatives of all cyanobacterial species, as representatives of all cyanobacterial species using a standard protocol as set out in (Golden, et al. 1987). Briefly, cells are harvested by centrifugation and re-suspended in BG-11 medium at a concentration of $2-5 \times 10^8$ cells per ml. To one ml of this cell solution the appropriate plasmid construct is added to a final concentration of 2-5 µg/ml. Cells were incubated in the dark for 8 hours followed by a 16 h light incubation prior to plating on BG-11 plates containing butafenacil or flumioxazin to select for the colonies that grow at the highest rates without affecting algal growth. Plates are incubated under the standard growth conditions (30° C., light intensity of 100 µmol photons $m^{-2} s^{-1}$). Butafenacil or flumioxazin resistant colonies were visible in 7-10 days. This is modified for each organism according to its needs, based on modifications of standard protocols.

EXAMPLE 11

Verification of the Presence of the Synthetic ppo Gene Transformed Algae and Cyanobacteria Harboring the Resistant Protoporphyrinogen Oxidase The transformants are replated on fresh agar medium containing $10^{-6}M$ or $10^{-7}M$ of butafenacil or flumioxazin, concentrations that have been shown to inhibit the wild-type algae growth as is shown in FIG. 11. Cells are allowed to generate to visible colonies. After incubation for a week the most resistant colonies are chosen. To ascertain gene transformation PCR analysis is preformed on wild type and butafenacil or flumioxazin resistant colonies.

A dose response curve is generated for the wild type alga and for the transformants. The wild types and the transformant algae are plated in their medium in 24 well plates with increasing concentrations of 0.1 µM, 0.3 µM, 0.5 µM butafenacil or flumioxazin. Algae are plated without the herbicide as a control. Transformants bearing the gene that confers resistance show ability to grow at higher concentrations than the wild type. The most resistant colonies are chosen for further analysis.

EXAMPLE 12

Prevention of Algae/Cyanobacteria Contaminants

To address the question of contaminants, the transformed algae are mixed with cyanobacteria such as *Synechococcus* PCC7002 and *Synechococcus* WH7803, which are known to overtake ponds. The transformant and the cyanobacteria are cultured alone and in mixed cultures with and without butafenacil or flumioxazin. The mixed culture is plated in a ratio of 10:1 transformant: cyanobacteria respectively. The cells are allowed to grow for one week in liquid culture, with daily removal of aliquots. These aliquots are counted under the microscope and the ratio of contaminants vs. algae is calculated. The mixed cultures (of transformants and contaminants) containing the herbicide show decreasing numbers of contaminants, whereas in the mixed cultures without the herbicide the cyanobacteria outcompete the algae.

EXAMPLE 13

Combination of Two Herbicide Types for Prevention of Algae/Cyanobacteria Contaminants To address the question of contaminants, stacked pds and ppo transformed algae are mixed together with wild type *Synechococcus* 7002 cyanobacteria, which are known to overtake ponds. The cells are allowed to grow together for 1 day to 1 week in liquid culture, with daily removal of aliquots that are plated either to new liquid culture or on Petri dishes with and without the combination of flurochloridone or fluridone and butafenacil or flumioxazin. Contaminant cyanobacteria vs. target algae are counted. Conditions are optimized for the competing organism, in order to verify that the transformed algae overcome outcompete the contamination under these conditions.

EXAMPLE 14

Prevention of Zooplankton Grazing by High $CO_2$ Concentrations and Herbicide Application To quantify $CO_2$ effects on plankton survivorship we incubate 81 L vessels of the algae *Pavlova lutheri, Isochrysis* CS-177, *Nannochloropsis oculata* CS-179, *Nannochloropsis like* CS-246, *Nannochloropsis salina* CS-190, *Tetraselmis suecica, Tetraselmis chuii* and *Nannochloris* sp or cyanobacteria *Synechococcus* PCC7002, *Synechococcus* WH-7803, *Thermosynechococcus elongatus* BP-1 with or without zooplankton (e.g. *Arthemia* sp.). The control and zooplankton treated containers are bubbled with air, 1%, 5% and 14% $CO_2$ together with specific herbicides that are applied at the appropriate concentrations. Algal cell density and zooplankton counts are done on each treatment over a 10 day period. Throughout the experiment pH is maintained at 7.0-8.0, which allows phytoplankton growth.

There is a near 100% reduction of live zooplankton in the >5% $CO_2$ and the herbicide treatments. Zooplankton are killed by the microtubule-inhibiting herbicides that do not harm the wild type algae and the cyanobacteria such as benefin, butralin, dinitramine, ethalfluralin, oryzalin, pendimethalin, trifluralin, amiprophos-methyl, butamiphos, dithiopyr, thiazopyr, propyzamide, tebutam and chlorthal-dimethyl. Algal density is significantly higher at 5 and 14% compared to ambient and 1% $CO_2$ concentrations. While zooplankton reduced algal growth at low concentrations, in high $CO_2$ there are no differences between batches with and without zooplankton, indicating the inhibition of zooplankton activity. Zooplankton numbers remain low for 7 days after termination of $CO_2$ treatments, implying a significant, long-term impact.

REFERENCES

Adams, E. E., J. A. Caulfield, et al. (1998). "Impacts of reduced pH from ocean $CO_2$ disposal: Sensitivity of zooplankton mortality to model parameters." *Waste Management* 17(5-6): 375-380.

Beale, S. I., Weinstein, J. D. (1990). "Biosynthesis of Heme and Chlorophylls." "in Tetrapyrrole Metabolism in Photosynthetic Organisms, ed. Dailey, H. A. (McGraw-Hill, New York), 287-391.

Böger, P. and G. Sandmann (1998). "Carotenoid biosynthesis inhibitor herbicides—mode of action and resistance mechanisms." *Pesticide Outlook* 9(6): 29-35.

Deng, M. D. and J. R. Coleman (1999). "Ethanol synthesis by genetic engineering in cyanobacteria." *Appl Environ Microbiol* 65(2): 523-8.

Golden, S. S., J. Brusslan, et al. (1987). "Genetic engineering of the cyanobacterial chromosome." *Methods Enzymol* 153: 215-31.

Gressel, J. and A. A. Levy (2006) Agriculture—the selector of improbable mutations. *Proceedings of the National Academy of Sciences USA* 103: 12215-12216

Grzebyk, D., O. Schofield, P. Falkowski, and J. Bernhard (2003) The Mesozoic radiation of eukaryotic algae: the portable plastid hypothesis. J. Phycol. 39:259-267)

Kindle, K, L., (1990). "High-frequency nuclear transformation of *Chlamydomonas reinhardtii.*" *Proc. Natl. Acad. Sci. USA* 87: 1228-1232.

Kurihara, H., A. Ishimatsu, et al. (2004). "Effects of elevated seawater $CO_2$ concentration on the meiofauna." *Journal of Marine Science and Technology*: 17-22.

Lermontova, I., Kruse, E., Mock, H. P. & Grimm, B. (1997). "Cloning and characterization of a plastidal and a mitochondrial isoform of tobacco protoporphyrinogen IX oxidase." Proc. Natl. Acad. Sci. USA 94, 8895-8900.

Lioudmila, A., Zaslayskaia, et al. (2000). "Transformation of the diatom phaeodactylum tricornutum (Bacillariophyceae) with a variety of selectable marker and reporter genes" *J. Phycol.* 36, 379-386.

Michel, A., R. S. Arias, et al. (2004). "Somatic mutation-mediated evolution of herbicide resistance in the nonindigenous invasive plant hydrilla (*Hydrilla verticillata*)." *Molecular Ecology* 13(10): 3229-3237.

Michel, A., Scheffler, B, E., et. al (2004). "Herbicide-resistant plants, and polynucleotides and methods for providing same." patent Application WO/2004/007691.

Patzoldt, W. L., Hager, A. G., et. al (2006). "A codon deletion confers resistance to herbicides inhibiting protoporphyrinogen oxidase." PNAS 33: 12329-12334.

Sheehan, J., T. Dunahay, et al. (2004). A Look Back at the US Department of Energy's Aquatic Species Program: Biodiesel from Algae; Close-Out Report, Island Press.

Sizova, I., Fuhrmann, M., et al. (2001). A *Streptomyces rimosus* aphVIII gene coding for a new type phosphotransferase provides stable antibiotic resistance to *Chlamydomonas reinhardtii*. *Gene* 277: 221-229.

Tranel, P, Hager, A., and Patzold, W. (2007) Herbicide Resistance Gene, Compositions and Methods. US patent Application, US 2007/0050863 A1

Watanabe, N., Che, F. S., Iwano, M., Takayama, S. &Yoshida, S. (2001). "Construction of an *Amaranthus hypochondriacus* Bacterial Artificial Chromosome Library and Genomic Sequencing of Herbicide Target Genes" J. Biol. Chem. 276, 20474-20481.

What is claimed is:

1. A method to maintain a cyanobacterial or algal monoculture free from unwanted species, said method comprising the steps of: a) Transforming a cyanobacterium or an alga with a nucleotide sequence to express resistance against one or more herbicides; b) Cultivating said cyanobacterium or alga expressing resistance against one or more herbicides; and c) adding one or more herbicides into the cultivation medium; wherein said alga or said cyanobacterium is transformed with a nucleotide sequence encoding for a protein conferring resistance to said one or more herbicides, wherein said protein has a sequence encoded according to the nucleotide sequence selected from the group consisting of SEQ ID NOs 1-6, 11 and 12.

2. The method of claim 1, wherein the herbicide is hydrophobic and is applied using a volatile organic solvent on an inner side of a polyethylene algae photobioreactor or pond liner.

3. The method of claim 1, wherein the herbicide is selected from the group consisting of fluorochloridone and fluridone.

4. The method of claim 1, wherein the alga is transformed with the nucleotide sequence selected from the group consisting of SEQ ID NO: 1, SEQ ID NO: 3 and SEQ ID NO:5.

5. The method of claim 4, wherein the nucleotide sequence is operably linked to a promoter selected from a group consisting of RbcS, fcpA, 35S, ubiquitin, tubulin and actin promoters.

6. The method of claim 1, wherein the cyanobacterium is transformed with the nucleotide sequence selected from the group consisting of SEQ ID NO:2, SEQ ID NO:4 and SEQ ID NO:6.

7. The method of claim 6, wherein the nucleotide sequence is operably linked to a promoter selected from a group consisting of RbcS, fcpA, 35S, ubiquitin, tubulin and actin promoters.

8. The method of claim 1, wherein the herbicide is butafenacil or flumioxazin.

9. The method of claim 1, wherein the alga is transformed with the nucleotide sequence SEQ ID NO:11.

10. The method of claim 1, wherein the sequence is operably linked to a promoter selected from a group consisting of RbcS, fcpA, 35S, ubiquitin, tubulin and actin promoters.

11. The method of claim 1, wherein the cyanobacterium is transformed with the nucleotide sequence SEQ ID NO:12.

12. The method of claim 11, wherein the sequence is operably linked to a promoter selected from a group consisting of RbcS, fcpA, 35S, ubiquitin, tubulin and actin promoters.

13. The method of claim 1, further comprising providing a $CO_2$ concentration of the cultivation media of between 5% and 100%.

14. The method of claim 1, wherein the cyanobacterium is selected from the group consisting of *Synechococcus* PCC7002, *Synechococcus* WH-7803, and *Thermosynechococcus elongatus* BP-1.

15. The method of claim 1, wherein the alga is selected from the group consisting of *Chlamydomonas reinhardtii*, *Pavlova lutheri, Isochrysis* CS-177, *Nanochloropsis* CS-179, *Nanochloropsis* CS-246, *Nanochloropsis salina* CS-190, *Tetraselmis suecica, Tetraselmis chuii* and *Nannochloris* sp.

16. The method of claim 1, wherein the transformation is performed through microporation.

* * * * *

SEQUENCE LISTING

```
<160> NUMBER OF SEQ ID NOS: 12

<210> SEQ ID NO 1
<211> LENGTH: 1743
<212> TYPE: DNA
<213> ORGANISM: Hydrilla sp
<220> FEATURE:
<221> NAME/KEY: misc_feature
<222> LOCATION: (1)..(1743)
<223> OTHER INFORMATION: Hydrilla phytoene desaturase with the histidine
      mutation according to the codon usage of Chlamydomonas

<400> SEQUENCE: 1
atgaccgtgg cccgcagcgt ggtggccgtg aacctgagcg gcagcctgca gaaccgctac      60
cccgccagca gcagcgtgtc ctgcttcctg ggcaaggagt accgctgcaa ctctatgctg     120
ggcttctgcg gcagcggcaa gctggccttc ggcgccaacg cccctactc caagatcgcc     180 gccaccaagc ccaagccgaa gctgcgcccc ctgaaggtga actgcatgga cttcccgcgc     240
ccggacatcg acaacaccgc caacttcctg gaggccgccg ccctgtcctc cagcttccgc     300
```

```
aacagcgccc gccccagcaa gcccctgcag gtggtgatcg ctggcgctgg cctggcgggc    360
ctgagcaccg ccaagtacct ggccgacgcc ggccacatcc ccatcctgct ggaggcccgc    420
gacgtgctgg cggcaaggt ggccgcctgg aaggacgacg acggcgactg gtacgagacc     480
ggcctgcaca tcttcttcgg cgcctacccc aacgtgcaga acctgttcgg cgagctgggc    540
atcaacgacc gcctgcagtg gaaggagcac agcatgatct cgccatgcc aacaagccc     600 ggcgagttca gccgcttcga cttccccgag gtgctgcccg ccccctgaa cggcatctgg     660 gccatcctga gaacaacga gatgctgacc tggcccgaga aggtgcagtt cgccatcggc    720
ctgctgcccg ccatgatcgg cggccagccc tacgtggagg cccaggacgg cctgaccgtg    780
caggagtgga tgcgcaagca gggcgtgccc gaccgcgtga acgacgaggt gttcatcgcc    840
atgagcaagg ccctgaactt catcaacccc gacgagctgt ccatgcagtg catcctgatc    900
gccctgaacc acttcctgca ggagaagcac ggcagcaaga tggccttcct ggacggcaac    960 cccccgagc gcctgtgcaa gccgatcgcc gaccacatcg agagcctggg cggccaggtg    1020
atcctgaaca ccgcatcca aagatcgag ctgaacgccg acaagagcgt gaagcacttc    1080
gtgctgacca acgcaacat catcaccggc gacgcctacg tgttcgccac ccccgtggac    1140
atcctgaagc tgctgctgcc cgaggactgg aaggagatca gctacttcaa gaagctggac    1200
aagctggtcg gcgtgcccgt gatcaacgtg cacatctggt tcgaccgcaa gctgaagaac    1260
acctacgacc acctgctgtt cagccgcagc ccctgctgt ccgtgtacgc cgacatgtcc     1320
gtgacctgca aggagtacta caaccccaac cagagcatgc tggagctggt gttcgccccc    1380
gccgagaagt ggatcagctg ctccgacagc gagatcatca acgccaccat gcaggagctg    1440
gccaagctgt tccccgacga gatcagcgcc gaccagagca aggccaagat cctgaagtac    1500
cacgtggtca agacccccg cagcgtgtac aagaccgtgc ccgactgcga gccctgccgc    1560 ccctgcagc gcagccccat cgagggcttc tacctggccg gcgactacac caagcagaag    1620
tacctggcga gcatggaggg cgccgtgctg tccggcaagc tgtgcgccca ggccatcgtg    1680
caggactgct ccctgctggc cagccgcgtg cagaagtccc cccagaccct gaccatcgcc    1740
taa                                                                 1743
```

<210> SEQ ID NO 2  
<211> LENGTH: 1740  
<212> TYPE: DNA  
<213> ORGANISM: Hydrilla sp  
<220> FEATURE:  
<221> NAME/KEY: misc_feature  
<222> LOCATION: (1)..(1740)  
<223> OTHER INFORMATION: Hydrilla phytoene desaturase with the histidine mutation according to the codon usage of cyanobacterium Synechococcus PCC7002

<400> SEQUENCE: 2

```
atgaccgtgg cccgctctgt ggtggccgtg aatctctctg gctctctcca aaatcgctat     60
cccgcctctt cttctgtgtc ttgttttctc ggcaaagaat atcgctgtaa ttctatgctc    120
ggcttttgtg gctctggcaa actcgccttt ggcgccaatg cccccctatt taaaattgcc    180
gccaccaaac ccaaacccaa actccgcccc ctcaaagtga attgtatgga ttttccccgc    240
cccgatattg ataataccgc caattttctc gaagccgccg ccctctcttc ttcttttcgc    300
aattctgccc gcccctctaa accctccaa gtggtgattg ccggcgccgg cctcgccggc    360
ctctctaccg ccaaatatct cgccgatgcc ggccacattc ccattctcct cgaagcccgc    420
gatgtgctcg gcggcaaagt ggccgcctgg aaagatgatg atggcgattg gtatgaaacc    480
```

```
ggcctccaca tttttttttgg cgcctatccc aatgtgcaaa atctctttgg cgaactcggc    540
attaatgatc gcctccaatg gaaagaacac tctatgattt ttgccatgcc caataaaccc    600
ggcgaatttt ctcgctttga tttttcccgaa gtgctcccccg ccccccctcaa tggcatttgg   660 gccattctca aaataatga aatgctcacc tggcccgaaa aagtgcaatt tgccattggc     720
ctcctccccg ccatgattgg cggccaaccc tatgtggaag cccaagatgg cctcaccgtg    780
caagaatgga tgcgcaaaca aggcgtgccc gatcgcgtga atgatgaagt gtttattgcc    840
atgtctaaag ccctcaattt tattaatccc gatgaactct ctatgcaatg tattctcatt    900
gccctcaatc actttctcca agaaaaacac ggctctaaaa tggcctttct cgatggcaat    960
ccccccgaac gcctctgtaa acccattgcc gatcacattg aatctctcgg cggccaagtg   1020
attctcaatt ctcgcattca aaaaattgaa ctcaatgccg ataaatctgt gaaacacttt   1080
gtgctcacca atggcaatat tattaccggc gatgcctatg tgtttgccac ccccgtggat   1140
attctcaaac tcctcctccc cgaagattgg aaagaaattt cttatttttaa aaaactcgat   1200 aaactcgtgg gcgtgcccgt gattaatgtg cacatttggt ttgatcgcaa actcaaaaat   1260
acctatgatc acctcctctt ttctcgctct cccctcctct ctgtgtatgc cgatatgtct   1320
gtgacctgta aagaatatta taatcccaat caatctatgc tcgaactcgt gtttgccccc   1380
gccgaaaaat ggatttcttg ttctgattct gaaattatta atgccaccat gcaagaactc   1440
gccaaactct ttcccgatga aatttctgcc gatcaatcta agccaaaat tctcaaatat    1500 cacgtggtga aaacccccgg ctctgtgtat aaaaccgtgc cgattgtga accctgtcgc   1560 cccctccaac gctctcccat tgaaggcttt tatctcgccg gcgattatac caaacaaaaa   1620
tatctcgcct ctatggaagg cgccgtgctc tctggcaaac tctgtgccca agccattgtg   1680
caagattgtt ctctcctcgc ctctcgcgtg caaaaatctc cccaaaccct caccattgcc   1740
```

<210> SEQ ID NO 3
<211> LENGTH: 1740
<212> TYPE: DNA
<213> ORGANISM: Hydrilla sp
<220> FEATURE:
<221> NAME/KEY: misc_feature
<222> LOCATION: (1)..(1740)
<223> OTHER INFORMATION: Hydrilla phytoene desaturase with the serine
      mutation according to the codon usage of Chlamydomonas

<400> SEQUENCE: 3

```
atgactgtag ctcgttctgt agtagctgta aacttatctg gttctttaca aaaccgttac    60
ccagcttctt cttctgtatc ttgtttctta ggtaaagaat accgttgtaa ctctatgtta   120
ggtttctgtg gttctggtaa attagctttc ggtgctaacg ctccatactc taaaattgct   180
gctactaaac caaaaccaaa attacgtcca ttaaaagtaa actgtatgga tttcccacgt   240
ccagatattg ataacactgc taacttctta gaagctgctg ctttatcttc ttctttccgt   300
aactctgctc gtccatctaa accattacaa gtagtaattg ctggtgctgg tttagctggt   360
ttatctactg ctaaatactt agctgatgct ggtcacattc aattttatt agaagctcgt   420 gatgtattag gtggtaaagt agctgcttgg aaagatgatg atggtgattg gtacgaaact   480
ggtttacaca ttttcttcgg tgcttaccca acgtacaaa acttattcgg tgaattaggt    540
attaacgatc gtttacaatg gaaagaacac tctatgattt tcgctatgcc aaacaaacca    600
ggtgaattct ctcgtttcga tttcccagaa gtattaccag ctccattaaa cggtatttgg    660 gctatttttaa aaacaacga aatgttaact tggccagaaa aagtacaatt cgctattggt   720
```

```
ttattaccag ctatgattgg tggtcaacca tacgtagaag ctcaagatgg tttaactgta      780
caagaatgga tgcgtaaaca aggtgtacca gatcgtgtaa acgatgaagt attcattgct      840
atgtctaaag ctttaaactt cattaaccca gatgaattat ctatgcaatg tattttaatt      900
gctttaaact ctttcttaca agaaaaacac ggttctaaaa tggctttctt agatggtaac      960
ccaccagaac gtttatgtaa accaattgct gatcacattg aatctttagg tggtcaagta     1020
atttttaaact ctcgtattca aaaaattgaa ttaaacgctg ataaatctgt aaaacacttc     1080
gtattaacta acgtaacat tattactggt gatgcttacg tattcgctac tccagtagat     1140
atttttaaaat tattattacc agaagattgg aaagaaattt cttacttcaa aaaattagat     1200
aaattagtag gtgtaccagt aattaacgta cacatttggt tcgatcgtaa attaaaaaac     1260
acttacgatc acttattatt ctctcgttct ccattattat ctgtatacgc tgatatgtct     1320
gtaacttgta agaatactca acccaaac caatctatgt tagaattagt attcgctcca     1380
gctgaaaaat ggatttcttg ttctgattct gaaattatta cgctactat gcaagaatta     1440
gctaaattat tcccagatga aatttctgct gatcaatcta agctaaaat tttaaaatac     1500
cacgtagtaa aaactccacg ttctgtatac aaaactgtac cagattgtga accatgtcgt     1560
ccattacaac gttctccaat tgaaggtttc tacttagctg gtgattacac taaacaaaaa     1620
tacttagctt ctatggaagg tgctgtatta tctggtaaat tatgtgctca agctattgta     1680
caagattgtt ctttattagc ttctcgtgta caaaaatctc cacaaacttt aactattgct     1740
```

<210> SEQ ID NO 4
<211> LENGTH: 1740
<212> TYPE: DNA
<213> ORGANISM: Hydrilla sp
<220> FEATURE:
<221> NAME/KEY: misc_feature
<222> LOCATION: (1)..(1740)
<223> OTHER INFORMATION: Hydrilla phytoene desaturase with the serine
      mutation according to the codon usage of the cyanobacterium
      Synechococcus PCC7002

<400> SEQUENCE: 4

```
atgaccgtgg cccgctctgt ggtggccgtg aatctctctg ctctctcca aaatcgctat       60
cccgcctctt cttctgtgtc ttgttttctc ggcaaagaat atcgctgtaa ttctatgctc      120
ggcttttgtg gctctggcaa actcgccttt ggcgccaatg cccctattc taaaattgcc      180
gccaccaaac ccaaacccaa actccgcccc ctcaaagtga attgtatgga ttttccccgc      240
cccgatattg ataataccgc caattttctc gaagccgccg ccctctcttc ttcttttcgc      300
aattctgccc gccctctaa accctccaa gtggtgattg ccggcgccgg cctcgccggc      360
ctctctaccg ccaaatatct cgccgatgcc ggccacattc ccattctcct cgaagcccgc      420
gatgtgctcg gcggcaaagt ggccgcctgg aaagatgatg atggcgattg gtatgaaacc      480
ggcctccaca tttttttttgg cgcctatccc aatgtgcaaa atctctttgg cgaactcggc      540
attaatgatc gcctccaatg gaaagaacac tctatgattt tgccatgcc aataaaccc      600
ggcgaatttt ctcgctttga ttttccccgaa gtgctccccg ccccccctcaa tggcatttgg      660
gccattctca aaaataatga aatgctcacc tggcccgaaa aagtgcaatt tgccattggc      720
ctcctccccg ccatgattgg cggccaaccc tatgtggaag cccaagatgg cctcaccgtg      780
caagaatgga tgcgcaaaca aggcgtgccc gatcgcgtga atgatgaagt gtttattgcc      840
atgtctaaag ccctcaattt tattaatccc gatgaactct ctatgcaatg tattctcatt      900
gccctcaatt cttttctcca agaaaaacac ggctctaaaa tggcctttct cgatggcaat      960
```

```
cccccccgaac gcctctgtaa acccattgcc gatcacattg aatctctcgg cggccaagtg    1020
attctcaatt ctcgcattca aaaaattgaa ctcaatgccg ataaatctgt gaaacacttt    1080
gtgctcacca atggcaatat tattaccggc gatgcctatg tgtttgccac ccccgtggat    1140
attctcaaac tcctcctccc cgaagattgg aaagaaattt cttatttaa aaaactcgat    1200
aaactcgtgg gcgtgcccgt gattaatgtg cacatttggt ttgatcgcaa actcaaaaat    1260
acctatgatc acctcctctt ttctcgctct ccctcctct ctgtgtatgc cgatatgtct    1320
gtgacctgta aagaatatta taatcccaat caatctatgc tcgaactcgt gtttgccccc    1380
gccgaaaaat ggatttcttg ttctgattct gaaattatta atgccaccat gcaagaactc    1440
gccaaactct ttcccgatga aatttctgcc gatcaatcta aagccaaaat tctcaaatat    1500
cacgtggtga aaccccccg ctctgtgtat aaaaccgtgc cgattgtga accctgtcgc    1560
cccctccaac gctctcccat gaaggctttt atctcgccg gcgattatac caaacaaaaa    1620
tatctcgcct ctatggaagg cgccgtgctc tctggcaaac tctgtgccca agccattgtg    1680
caagattgtt ctctcctcgc ctctcgcgtg caaaaatctc cccaaaccct caccattgcc    1740

<210> SEQ ID NO 5
<211> LENGTH: 1740
<212> TYPE: DNA
<213> ORGANISM: Hydrilla sp
<220> FEATURE:
<221> NAME/KEY: misc_feature
<222> LOCATION: (1)..(1740)
<223> OTHER INFORMATION: Hydrilla phytoene desaturase with the cysteine
      mutation according to the codon usage of Chlamydomonas

<400> SEQUENCE: 5
atgactgtag ctcgttctgt agtagctgta aacttatctg gttctttaca aaaccgttac      60
ccagcttctt cttctgtatc ttgtttctta ggtaaagaat accgttgtaa ctctatgtta     120
ggtttctgtg gttctggtaa attagctttc ggtgctaacg ctccatactc taaaattgct     180
gctactaaac caaaaccaaa attacgtcca ttaaaagtaa actgtatgga tttcccacgt     240
ccagatattg ataacactgc taacttctta gaagctgctg cttttatctc ttctttccgt     300
aactctgctc gtccatctaa accattacaa gtagtaattg ctggtgctgg tttagctggt     360
ttatctactg ctaaatactt agctgatgct ggtcacattc aattttatt agaagctcgt     420
gatgtattag gtggtaaagt agctgcttgg aaagatgatg atggtgattg gtacgaaact     480
ggtttacaca ttttcttcgg tgcttaccca aacgtacaaa acttattcgg tgaattaggt     540
attaacgatc gtttacaatg gaaagaacac tctatgattt cgctatgcc aaacaaacca     600
ggtgaattct ctcgtttcga tttcccagaa gtattaccag ctccattaaa cggtatttgg     660
gctatttaa aaaacaacga aatgttaact tggccagaaa agtacaatt cgctattggt     720
ttattaccag ctatgattgg tggtcaacca tacgtagaag ctcaagatgg tttaactgta     780
caagaatgga tgcgtaaaca aggtgtacca gatcgtgtaa acgatgaagt attcattgct     840
atgtctaaag ctttaaactt cattaaccca gatgaattat ctatgcaatg tattttaatt     900
gctttaaact gtttcttaca agaaaaacac ggttctaaaa tggctttctt agatggtaac     960
ccaccagaac gtttatgtaa accaattgct gatcacattg aatctttagg tggtcaagta    1020
attttaaact ctcgtattca aaaaattgaa ttaacgctg ataaatctgt aaaacacttc    1080
gtattaacta cggtaacat tattactggt gatgcttacg tattcgctac tccagtagat    1140
attttaaaat tattaccc agaagattgg aagaaattt cttacttcaa aaaattgat    1200
aaattagtag gtgtaccagt aattaacgta cacatttggt tcgatcgtaa attaaaaaac    1260
```

| acttacgatc acttattatt ctctcgttct ccattattat ctgtatacgc tgatatgtct | 1320 |
| gtaacttgta aagaatacta caacccaaac caatctatgt tagaattagt attcgctcca | 1380 |
| gctgaaaaat ggatttcttg ttctgattct gaaattatta cgctactat gcaagaatta | 1440 |
| gctaaattat tcccagatga aatttctgct gatcaatcta aagctaaaat tttaaaatac | 1500 |
| cacgtagtaa aaactccacg ttctgtatac aaaactgtac cagattgtga accatgtcgt | 1560 |
| ccattacaac gttctccaat tgaaggtttc tacttagctg gtgattacac taaacaaaaa | 1620 |
| tacttagctt ctatggaagg tgctgtatta tctggtaaat tatgtgctca agctattgta | 1680 |
| caagattgtt ctttattagc ttctcgtgta caaaaatctc cacaaacttt aactattgct | 1740 |

<210> SEQ ID NO 6
<211> LENGTH: 1740
<212> TYPE: DNA
<213> ORGANISM: Hydrilla sp
<220> FEATURE:
<221> NAME/KEY: misc_feature
<222> LOCATION: (1)..(1740)
<223> OTHER INFORMATION: Hydrilla phytoene desaturase with the cysteine
      mutation according to the codon usage of the cyanobacterium
      Synechococcus PCC7002

<400> SEQUENCE: 6

| atgaccgtgg cccgctctgt ggtggccgtg aatctctctg ctctctccaa aaatcgctat | 60 |
| cccgcctctt cttctgtgtc ttgttttctc ggcaaagaat atcgctgtaa ttctatgctc | 120 |
| ggcttttgtg gctctggcaa actcgccttt ggcgccaatg ccccctattc taaaattgcc | 180 |
| gccaccaaac ccaaacccaa actccgcccc ctcaaagtga attgtatgga ttttccccgc | 240 |
| cccgatattg ataataccgc caattttctc gaagccgccg ccctctcttc ttcttttcgc | 300 |
| aattctgccc gccccctctaa acccctccaa gtggtgattg ccggcgccgg cctcgccggc | 360 |
| ctctctaccg ccaaatatct cgccgatgcc ggccacattc ccattctcct cgaagcccgc | 420 |
| gatgtgctcg gcggcaaagt ggccgcctgg aaagatgatg atggcgattg gtatgaaacc | 480 |
| ggcctccaca ttttttttgg cgcctatccc aatgtgcaaa atctctttgg cgaactcggc | 540 |
| attaatgatc gcctccaatg gaaagaacac tctatgattt ttgccatgcc caataaaccc | 600 |
| ggcgaatttt ctcgctttga ttttccccgaa gtgctccccg ccccccctcaa tggcatttgg | 660 |
| gccattctca aaaataatga aatgctcacc tggcccgaaa agtgcaatt tgccattggc | 720 |
| ctcctccccg ccatgattgg cggccaaccc tatgtggaag cccaagatgg cctcaccgtg | 780 |
| caagaatgga tgcgcaaaca aggcgtgccc gatcgcgtga tgatgaagt gtttattgcc | 840 |
| atgtctaaag ccctcaatttt tattaatccc gatgaactct ctatgcaatg tattctcatt | 900 |
| gccctcaatt gttttctcca agaaaaacac ggctctaaaa tggcctttct cgatggcaat | 960 |
| cccccgaac gcctctgtaa acccattgcc gatcacattg aatctctcgg cggccaagtg | 1020 |
| attctcaatt ctcgcattca aaaaattgaa ctcaatgccg ataaatctgt gaaacacttt | 1080 |
| gtgctcacca atggcaatat tattaccggc gatgcctatg tgtttgccac ccccgtggat | 1140 |
| attctcaaac tcctcctccc cgaagattgg aaagaaattt cttatttaa aaaactcgat | 1200 |
| aaactcgtgg gcgtgcccgt gattaatgtg cacatttggt ttgatcgcaa actcaaaaat | 1260 |
| acctatgatc acctcctctt ttctcgctct cccctcctct ctgtgtatgc cgatatgtct | 1320 |
| gtgacctgta aagaatatta taatcccaat caatctatgc tcgaactcgt gtttgccccc | 1380 |
| gccgaaaaat ggatttcttg ttctgattct gaaattatta tgccaccat gcaagaactc | 1440 |
| gccaaactct ttcccgatga aatttctgcc gatcaatcta aagccaaaat tctcaaatat | 1500 |

-continued

```
cacgtggtga aaaccccccg ctctgtgtat aaaaccgtgc ccgattgtga accctgtcgc    1560
cccctccaac gctctcccat tgaaggcttt tatctcgccg gcgattatac caaacaaaaa    1620
tatctcgcct ctatggaagg cgccgtgctc tctggcaaac tctgtgccca agccattgtg    1680
caagattgtt ctctcctcgc ctctcgcgtg caaaaatctc cccaaaccct caccattgcc    1740
```

```
<210> SEQ ID NO 7
<211> LENGTH: 20
<212> TYPE: DNA
<213> ORGANISM: Artificial
<220> FEATURE:
<223> OTHER INFORMATION: Chemically synthetized
<220> FEATURE:
<221> NAME/KEY: misc_feature
<222> LOCATION: (1)..(20)
<223> OTHER INFORMATION: pSI103-1362 primer

<400> SEQUENCE: 7
aatgcaagca gttcgcatgc                                                  20

<210> SEQ ID NO 8
<211> LENGTH: 18
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(18)
<223> OTHER INFORMATION: PDS reverse primer

<400> SEQUENCE: 8
ggcgatggtc agggtctg                                                    18

<210> SEQ ID NO 9
<211> LENGTH: 20
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(20)
<223> OTHER INFORMATION: PDS F short primer

<400> SEQUENCE: 9
cgtggtggcc gtgaacctga                                                  20

<210> SEQ ID NO 10
<211> LENGTH: 20
<212> TYPE: DNA
<213> ORGANISM: artificial
<220> FEATURE:
<223> OTHER INFORMATION: chemically synthetized
<220> FEATURE:
<221> NAME/KEY: misc_feature
<222> LOCATION: (1)..(20)
<223> OTHER INFORMATION: PDS R short primer

<400> SEQUENCE: 10
cgctgttgcg gaagctggag                                                  20

<210> SEQ ID NO 11
<211> LENGTH: 1602
<212> TYPE: DNA
<213> ORGANISM: Amarathus tuberculatus
<220> FEATURE:
<221> NAME/KEY: misc_feature
```

<222> LOCATION: (1)..(1602)
<223> OTHER INFORMATION: Amaranthus tuberculatus protoporphyrinogen
      oxidase gene according to the codon usage of Chlamydomonas
      reinhardtii

<400> SEQUENCE: 11

```
atggtcatcc agtccattac tcatctgagc cctaacctgg ccctgccgtc gcccctgtcc      60
gtgtcgacca agaactaccc tgtggcggtg atgggcaaca tcagcgagcg cgaggagccc     120
acgagcgcca agcgcgtggc cgtggtgggt gccggtgtca gcggcctggc ggctgcctac     180
aagctgaaga gccacggcct gagcgtgacc ctgttcgagg cggactcgcg ggcgggcggc     240
aagctcaaga cggtgaagaa ggacggcttc atctgggacg agggcgccaa cactatgacg     300
gagtccgagg cggaggtgtc cagcctgatc gacgatctcg gcctgcgcga gaagcagcag     360
ctgcccatta gccagaacaa gcgctacatt gctcgcgacg gcctgccggt gctgctgccc     420
tcgaaccctg ccgcgctgct gacctccaac atcctgtcgg ccaagtccaa gctgcagatc     480
atgctggagc cctttctgtg gcgcaagcac aacgccaccg agctgtcgga cgagcacgtc     540
caagagtccg tgggcgagtt cttcgagcgg cactttggca aggagttcgt cgattacgtc     600
atcgacccgt tcgtggccgg gacgtgcggc gacccccagt ccctgagcat gcaccacacg     660
ttccccgagg tgtggaacat cgagaagcgc tttgggtcgg tgttcgctgg cctgatccag     720
tcgaccctcc tgtcgaagaa ggagaagggc ggcgagaacg cgtccattaa gaagccgcgc     780
gtgcgcggct cgttcagctt ccagggcggc atgcagacgc tggtggacac catgtgcaag     840
cagctggggg aggacgagct gaagctgcaa tgcgaggtcc tctcgctgag ctacaaccag     900
aagggcatcc ccagcctggg caactggtcc gtgtcgagca tgtccaacaa cacctcggag     960
gaccagtcct acgacgccgt ggtcgtgacc gcgccgatcc gcaacgtgaa ggagatgaag    1020
atcatgaagt tcggcaaccc gttcagcctg gacttcatcc ctgaggtgac gtacgtgccc    1080
ctcagcgtga tgatcaccgc gttcaagaag gacaaggtca agcgcccgct ggagggtttc    1140
ggggtcctga tccccagcaa ggagcagcac aacggcctca agaccctggg caccctgttc    1200
tcgtccatga tgttccccga ccgggcgccg agcgacatgt gcctgttcac tacgttcgtg    1260
ggcggcagcc gcaaccgcaa gctggccaac gccagcaccg acgagctcaa gcagatcgtg    1320
tccagcgatc tccagcagct gctgggcacc gaggatgagc cctccttcgt gaaccacctg    1380
ttttggagca acgctttccc gctgtacggc cataactacg actgcgtgct gcgggcgatt    1440
gacaagatgg agaaggacct gcccggcttc ttctacgcgg gtaaccacaa gggcggcctg    1500
tcggtgggga aggcgatggc ctccggttgc aaggctgccg agctggtcat cagctacctc    1560
gactcgcaca tctatgtgaa gatggacgag aagaccgcct ga                       1602
```

<210> SEQ ID NO 12
<211> LENGTH: 1599
<212> TYPE: DNA
<213> ORGANISM: Amarathus tuberculatus
<220> FEATURE:
<221> NAME/KEY: misc_feature
<222> LOCATION: (1)..(1599)
<223> OTHER INFORMATION: Amaranthus tuberculatus protoporphyrinogen
      oxidase gene according to the codon usage of the cyanobacterium
      Synechococcus. PCC7002

<400> SEQUENCE: 12

```
atggtgattc aaagtattac ccatctcagt cccaatctcg ccctccccag tcccctcagt      60
gtgagtacca aaaattatcc cgtggccgtg atgggcaata ttagtgaacg cgaagaaccc     120
accagtgcca aacgcgtggc cgtggtgggc gccggcgtga gtggcctcgc cgccgcctat     180
```

```
aaactcaaaa gtcatggcct cagtgtgacc ctctttgaag ccgatagtcg cgccggcggc      240
aaactcaaaa ccgtgaaaaa agatggcttt atttgggatg aaggcgccaa taccatgacc      300
gaaagtgaag ccgaagtgag tagtctcatt gatgatctcg gcctccgcga aaaacaacaa      360
ctccccatta gtcaaaataa acgctatatt gcccgcgatg gcctccccgt gctcctcccc      420
agtaatcccg ccgccctcct caccagtaat attctcagtg ccaaaagtaa actccaaatt      480
atgctcgaac cctttctctg gcgcaaacat aatgccaccg aactcagtga tgaacatgtg      540
caagaaagtg tgggcgaatt ttttgaacgc cattttggca agaatttgt ggattatgtg       600 attgatccct ttgtggccgg cacctgtggc gatccccaaa gtctcagtat gcatcatacc      660
tttcccgaag tgtggaatat tgaaaaacgc tttggcagtg tgtttgccgg cctcattcaa      720
agtaccctcc tcagtaaaaa agaaaaaggc ggcgaaaatg ccagtattaa aaaacccgc       780 gtgcgcggca gttttagttt tcaaggcggc atgcaaaccc tcgtggatac catgtgtaaa      840
caactcggcg aagatgaact caaactccaa tgtgaagtgc tcagtctcag ttataatcaa      900
aaaggcattc ccagtctcgg caattggagt gtgagtagta tgagtaataa taccagtgaa      960
gatcaaagtt atgatgccgt ggtggtgacc gcccccattc gcaatgtgaa agaaatgaaa     1020
attatgaaat ttggcaatcc ctttagtctc gattttattc ccgaagtgac ctatgtgccc     1080
ctcagtgtga tgattaccgc cttttaaaaaa gataaagtga aacgcccccct cgaaggcttt     1140 ggcgtgctca ttcccagtaa agaacaacat aatggcctca aaaccctcgg caccctcttt     1200
agtagtatga tgtttcccga tcgcgccccc agtgatatgt gtctctttac caccttttgtg     1260 ggcggcagtc gcaatcgcaa actcgccaat gccagtaccg atgaactcaa acaaattgtg     1320
agtagtgatc tccaacaact cctcggcacc gaagatgaac ccagttttgt gaatcatctc     1380 tttttggagta atgccttttcc cctctatggc cataattatg attgtgtgct ccgcgccatt     1440
gataaaatgg aaaaagatct cccccggcttt ttttatgccg gcaatcataa aggcggcctc     1500
agtgtgggca aagccatggc cagtggctgt aaagccgccg aactcgtgat tagttatctc     1560
gatagtcata tttatgtgaa aatggatgaa aaaaccgcc                            1599
```